United States Patent [19]
Skulnick

[11] 4,171,431
[45] Oct. 16, 1979

[54] NUCLEOSIDES AND PROCESS

[75] Inventor: Harvey I. Skulnick, Oshtemo Township, Kalamazoo County, Mich.

[73] Assignee: The Upjohn Company, Kalamazoo, Mich.

[21] Appl. No.: 802,555

[22] Filed: Jun. 1, 1977

Related U.S. Application Data

[63] Continuation-in-part of Ser. No. 715,664, Aug. 19, 1976, abandoned.

[51] Int. Cl.² ............................................. C07H 17/00
[52] U.S. Cl. ..................................... 536/23; 424/180; 544/223; 544/194; 544/220; 536/29
[58] Field of Search ........................................... 536/23

[56] References Cited

U.S. PATENT DOCUMENTS

| | | | |
|---|---|---|---|
| 3,708,469 | 1/1973 | Vorbruggan et al. | 536/23 |
| 3,721,664 | 3/1973 | Hoffer | 536/23 |
| 3,748,320 | 7/1973 | Vorbruggan et al. | 536/23 |
| 3,817,980 | 6/1974 | Vorbruggen et al. | 536/23 |
| 3,907,779 | 9/1975 | DoBoa et al. | 536/23 |

Primary Examiner—Johnnie R. Brown
Assistant Examiner—Blondel Hazel
Attorney, Agent, or Firm—William G. Jameson

[57] ABSTRACT

Novel 5,6-dihydro-syn(s)-triazine nucleosides and nucleotides and a novel process for preparing the same. The novel nucleosides and nucleotides are disclosed as active in vitro and/or in vivo against susceptible DNA viruses.

18 Claims, 1 Drawing Figure

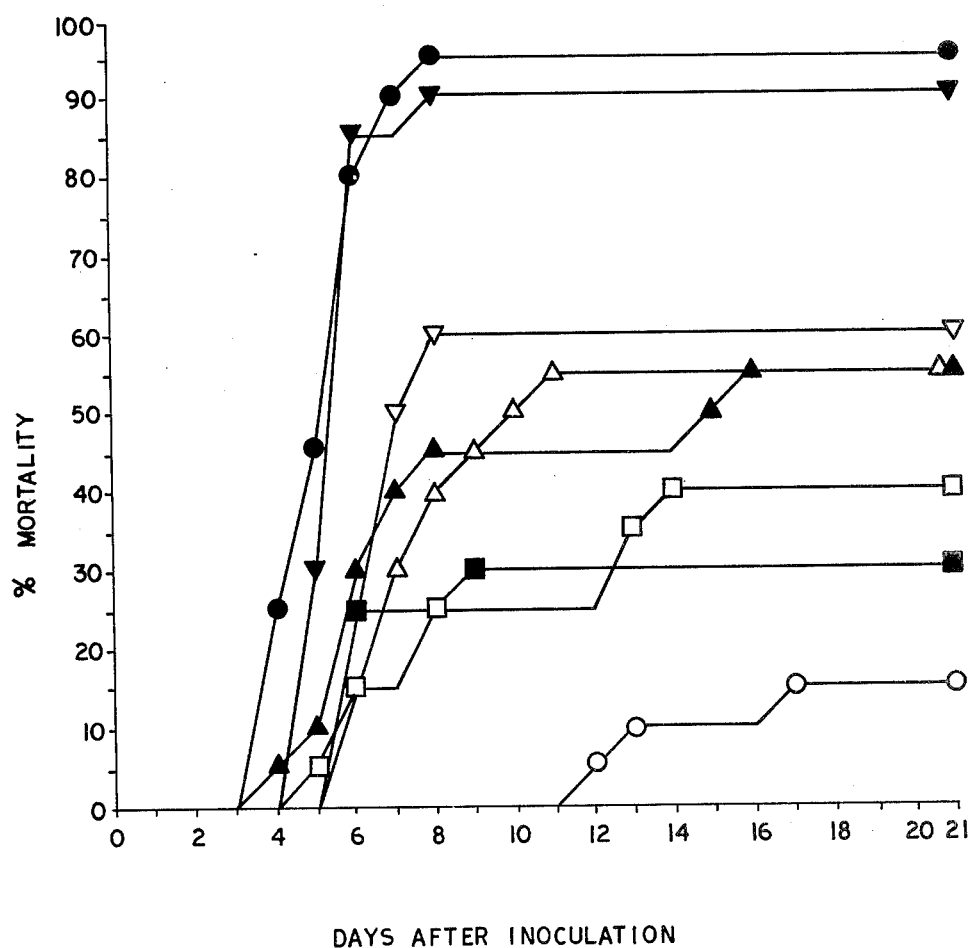
TABLE 1
| | | MST | %S |
|---|---|---|---|
| ● SALINE | | 6.3 | 5 |
| ○ U44590 | 400 mg./kg. | 20.8 | 85 |
| □ U44590 | 200 | 16.8 | 60 |
| △ U44590 | 100 | 14.2 | 45 |
| ▽ U44590 | 50 | 12.8 | 40 |
| ■ U50365 | 200 | 17.4 | 70 |
| ▲ U50365 | 100 | 14.2 | 45 |
| ▼ U50365 | 50 | 7.4 | 10 |
DAYS AFTER INOCULATION

NUCLEOSIDES AND PROCESS

CROSS REFERENCE TO RELATED APPLICATION

This application is a continuation-in-part of my co-pending application Ser. No. 715,664, filed Aug. 19, 1976 now abandoned.

BACKGROUND OF THE INVENTION

U.S. Pat. No. 3,907,779 issued Sept. 23, 1975 describes and claims the compound 1-(2-deoxy-β-D-ribofuranosyl)-5-methyl-5,6-dihydro-s-triazine-2,4-(1H,3H)-dione and various derivatives thereof.

U.S. Pat. No. 3,907,779 describes the original discovery, identification, and production of 1-(2-deoxy-β-D-ribofuranosyl)-5-methyl-5,6-dihydro-s-triazine-2,4-(1H,3H)-dione by the controlled fermentation of the microorganism *Streptomyces platensis* var. *clarensis*, NRRL 8035.

The novel compounds of this invention have not been produced by the controlled fermentation of the microorganism NRRL 8035, and it is not clear how this objective might be accomplished with the microorganism.

U.S. Pat. No. 3,708,469 issued Jan. 2, 1973 describes the silylation extension of the Hilbert-johnson reaction for the production of 2-thiopyrimidine nucleosides. Winkley and Robins, J. Org. Chem. 35, pp. 491-496 (1970) utilized the bis-trimethylsilyl derivative of 4-amino-s-triazine-2-(1H)-one for reaction with blocked ribofuranosyl halides.

In this invention, the Hilbert-Johnson reaction is modified to the use of the mono-silylated or disilylated 5,6-dihydro-s-triazines which are non-aromatic, and an optimal temperature range between minus (−) 25° C. and 25° C. is disclosed. None of the prior art references disclose a silylated non-aromatic sym-triazinone base for reaction with a blocked-pentofuranosyl halide. More specifically, none of the prior art references disclose the use of a monosilylated non-aromatic sym-triazinone base for this reaction.

BRIEF SUMMARY OF THE INVENTION

This invention pertains to new organic chemical compounds and a process for preparing the same. The invention is more particularly directed to new 1-(2-deoxy-β-D-pentofuranosyl)-5,6-dihydro-s-triazines prepared by reacting a 3',5'-di-O-blocked (e.g. acylated)-2-deoxypentofuranosyl halide with a silylated 5,6-dihydro-s-triazine base. The scope of this invention encompasses the 3',5'-blocked nucleosides, the 3'-blocked nucleosides, the 5'-blocked nucleosides, and the free nucleosides as precursors, intermediates, and final products. The corresponding nucleotides are also disclosed.

This invention also comprises an improved process for preparing the compounds of the invention, as well as a non-microbiological process for preparing the compound 1-(2-deoxy-β-D-ribofuranosyl)-5-methyl-5,6-dihydro-s-triazine-2,4-(1H,3H)-dione.

DETAILED DESCRIPTION OF THE INVENTION

In accordance with this invention, the 5,6-dihydro-s-triazine nucleosides and nucleotides are represented by structure Ia

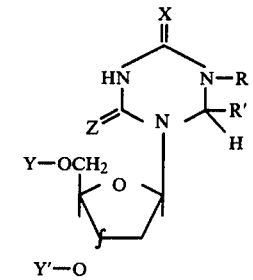

wherein it is understood that Ia can exist in tautomeric forms such as Ib and Ic and that the compounds of this invention are likely to be mixtures of all tautomeric forms, the percentages of each tautomer to be at least partially dependent on the nature of X, R, R', Z, Y and Y', and the physical environment of the compound

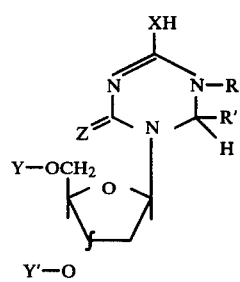

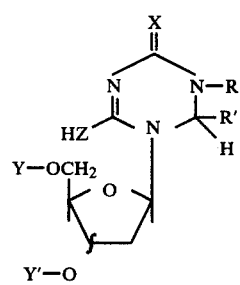

For the purpose of brevity throughout the application and claims, the compounds will be referred to hereinafter in their tautomeric form, corresponding to structure Ia.

The X substituent is selected from the group consisting of oxygen, imino, lower-alkylimino, and lower-acylimino; R' is selected from the group consisting of hydrogen and loweralkyl; Y is selected from the group consisting of hydrogen, carboxacyl of from 1 through 18 carbon atoms, and phosphono; Y' is selected from the group consisting of carboxacyl and hydrogen; Z is selected from the group consisting of oxygen and sulfur; R is selected from the group consisting of hydrogen, lower-alkyl, phenyl, benzyl, cyclopropyl, lower-alkoxylower-alkyl, and lower-alkylthiolower-alkyl with the proviso that when R' is hydrogen, X and Z are oxygen, Y is hydrogen, carboxacyl of from 1 through 18 carbon atoms or phosphono, and Y'-O is in the erythro position, then R is hydrogen, lower alkyl of 2 through 4 carbon atoms, phenyl, benzyl, cyclopropyl, lower-alkoxylower-alkyl, or lower-alkylthiolower-alkyl; and pharmaceutically acceptable salts thereof when X is imino or lower-alkylimino or when Y is phosphono.

The wavy line joining Y'—O to the body of the molecule as shown in formula 1a indicates that the Y'—O may be in either the erythro or threo configuration.

The term "carboxacyl" as used through the specification and claims means the acyl radical of a hydrocarbon carboxylic acid having from 1 to 18 carbon atoms, inclusive, or of a hydrocarbon carboxylic acid substituted with an inert group. Representative of such carboxacyl groups are those of the formula:

wherein E is hydrocarbyl of from 1 to 17 carbon atoms, inclusive, or hydrocarbyl of from 1 to 17 carbon atoms, inclusive, wherein a hydrogen atom has been replaced with an inert substituent group. Illustrative of acyl radicals of a hydrocarbon carboxylic acid wherein E is hydrocarbyl are the acyl radicals of (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric stearic, acrylic, crotonic, undecylenic, oleic, hexynoic, heptynoic, octynoic acids and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexenecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, 2-methylbutylbenzoic acid, and the like; and (e) aromatic aliphatic carboxylic acids, for example, phenylacetic acid, phenylpropionic acid, phenylvaleric acid, cinnamic acid, phenylpropionic acid, and naphthylacetic acid, and the like.

The term "hydrocarbon carboxylic acid substituted with an inert group" is used herein to mean a hydrocarbon carboxylic acid wherein one or more hydrogen atoms attached directly to a carbon atom have been replaced with a group inert to reaction under the conditions hereinafter described for preparing compounds (1) of the invention. Illustrative of such substituent groups are halo-, nitro-, hydroxy-, carboxy-, amino-, cyano-, thiocyanato-, or alkoxy-groups. Illustrative of halo-, nitro-, hydroxy-, carboxy-, amino-, cyano-, thiocyanato- and alkoxy- substituted hydrocarbon carboxylic acids are mono-, di, and trichloroacetic acid; α- and β- chloropropionic acid; α- and γ-bromobutyric acid; α- and δ-iodovaleric acid; mevalonic acid; 2- and 4-chlorocyclohexanecarboxylic acid; shikimic acid; 2-nitro-1-methylcyclobutanecarboxylic acid; 1,2,3,4,5,6-hexachloro cyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylcyclohexanecarboxylic acid; 3-bromo-3-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcyclohexanecarboxylic acid; homogentisic acid; 0-, m-, and p-chlorobenzoic acid; anisic acid; salicylic acid; p-hydroxybenzoic acid; β-resorcylic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acids; 2,4,6-trinitrobenzoic acid; thiocyanoacetic acid; cyanopropionic acid; lactic acid; ethoxyformic acid (ethyl hydrogen carbonate); butyloxyformic acid; pentyloxyformic acid; hexyloxyformic acid; dodecyloxyformic acid; hexadecyloxyformic acid; malonic acid; succinic acid; glutaric acid and the like.

The term "lower alkyl" is employed in its usual sense as meaning alkyl of from 1 to 4 carbon atoms, inclusive, such as methyl, ethyl, propyl, butyl and isomeric forms thereof.

The term "lower-alkoxylower-alkyl" as used throughout the specification and claims means lower alkyl of from 1 to 4 carbon atoms, inclusive, substituted by alkoxy of 1 to 4 carbon atoms, inclusive.

Illustrative of lower-alkoxylower-alkyl are methoxymethyl, ethoxymethyl, propoxymethyl, 2-ethoxyethyl, 1-ethoxyethyl and the like.

The term "lower-alkylthiolower-alkyl" as used throughout the specification and claims means lower alkyl of from 1 to 4 carbon atoms, inclusive, substituted by alkylthio of from 1 to 4 carbon atoms.

Illustrative of lower-alkylthiolower-alkyl are methylthiomethyl, ethylthiomethyl, propylthiomethyl, 2-methylthioethyl, 1-methylthioethyl, 2-ethylthioethyl, 4-methylthiobutyl and the like.

The term "loweracylimino" as used herein means an imine function substituted by an acyl radical of from 1 to 4 carbon atoms, inclusive.

Illustrative of loweracylimino are acetylimino, n-butyroylimino, and the like.

The term "pharmaceutically acceptable salts" as used throughout the specification and claims means all pharmaceutically acceptable salts of the compounds, including, for example, acid addition salts of compounds of formula 1a such as hydrochloride, sulfate, acetate and the like, when X is imino or lower-alkylimino; as well as salts derived from the phosphate function when Y is phosphono, such as sodium, potassium, calcium and ammonium salts thereof. The pharmaceutically acceptable salts can be used in the same manner as the free base and can be prepared by methods well known in the art.

The free nucleosides of the invention, compounds according to formula 1a wherein Y and Y' are hydrogen, are active in vitro against various susceptible DNA viruses, for example, susceptible Herpes viruses, including the Herpes simplex type I virus, and thus can be used to inhibit the growth of susceptible DNA viruses in tissue culture medium at a concentration of from about 25 to about 200 mcg/ml. the free nucleosides of the invention, compounds according to formula 1a wherein Y and Y' are hydrogen, can also be used in an in vitro screening system to determine the presence of susceptible DNA viruses.

The acyl derivatives of the free nucleosides of the invention, compounds according to formula 1a wherein Y and/or Y' are carboxacyl, can be used, advantageously, to upgrade the free nucleosides. This is accomplished by acylating the free nucleosides, recovering the acylated compound relatively free of impurities, then deacylating the acylated free nucleoside to give the free nucleoside in a more purified form.

Further, the acyl derivatives of free nucleosides of the invention, compounds according to formula 1a wherein Y and Y' are carboxyacyl, can be used for the same antiviral purposes as the free nucleosides of the invention.

The 5'-phosphate of the free nucleosides can be used for the same purposes as the free nucleosides.

In addition, compounds of the formula 2

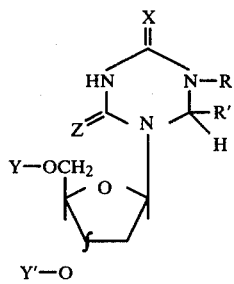

2 wherein the X substituent is selected from the group consisting of oxygen, imino, lower-alkylimino, and lower-acylimino; R' is selected from the group consisting of hydrogen and loweralkyl; Y is selected from the group consisting of hydrogen, carboxyacyl of from 1 through 18 carbon atoms, and phosphono; Y' is selected from the group consisting of carboxacyl and hydrogen; Z is selected from the group consisting of oxygen and sulfur; R is selected from the group consisting of hydrogen, methyl, ethyl, n-propyl, isopropyl, phenyl, benzyl, cyclopropyl, lower-alkoxylower-alkyl, and lower-alkylthiolower-alkyl with the proviso that when R' is hydrogen, X and Z are oxygen, Y is hydrogen, carboxyacyl of from 1 through 18 carbon atoms or phosphono, and Y'—O is in the erythro position, then R is hydrogen, ethyl, n-propyl, isopropyl, phenyl, benzyl, cyclopropyl, lower-alkoxy lower-alkyl, or lower-alkylthiolower-alkyl; and pharmaceutically acceptable salts thereof when X is imino or lower-alkylimino or when Y is phosphono, can be used to treat susceptible DNA viral infections in humans and animals, such as those due to susceptible herpes virus. Herpes viruses include, for example herpes simplex type 1, herpes simplex type 2, varicella zoster and cytomegalovirus, as well as equine abortion virus, infectious bovine rhinotracheitis virus, Marek's disease virus, canine herpes virus and feline rhinotracheitis virus. However, some Herpes viruses such as pseudorabies and equine abortion virus have been tested in vitro against 1-(2-deoxy-β-D-ribofuranosyl)-5-methyl-5,6-dihydro-s-triazine-2,4-(1H,3H)-dione and 1-(2-deoxy-β-D-ribofuranosyl)-5-ethyl-5,6-dihydro-s-triazine-2,4-(1H,3H)-dione and, to date, have been demonstrated to be refractory or at best only slightly inhibited, i.e. susceptible. To date, treatment of vaginal herpes simplex virus type 2 infection in mice with 1-(2-deoxy-β-D-ribofuranosyl)-5-methyl-5,6-dihydro-s-triazine-2,4-(1H,3H)-dione or 1-(2-deoxy-β-D-ribofuranosyl)-5-ethyl-5,6-dihydro-s-triazine-2,4-(1H,3H)-dione, given by subcutaneous injection at doses such as those shown in Table 1, page 62 has resulted in extensions of mean survival times but the number of mice surviving the infection was not greatly or significantly enhanced. Herpes simplex type 2 virus (HSV-2) has been tested in vitro against 1-(2-deoxy-β-D-ribofuranosyl)-5-methyl-5,6-dihydro-s-triazine-2,4-(1H,3H)-dione, 1-(2-deoxy-β-D-ribofuranosyl)-5-ethyl-5,6-dihydro-s-triazine-2,4-(1H,3H)-dione, 1-(2-deoxy-β-D-ribofuranosyl)-5-n-propyl-5,6-dihydro-s-triazine-2,4-(1H,3H)-dione, 1-(2-deoxy-β-D-riboruranosyl)-5-isopropyl-5,6-dihydro-s-triazine-2,4-(1H,3H)-dione, 1-(2-deoxy-β-D-ribofuranoxyl-5-cyclopropyl-5,6-dihydro-s-triazine-2,4-(1H,3H)-dione, 1-(2-deoxy-β-D-ribofuranosyl)-5-n-butyl-5,6-dihydro-s-triazine-2,4-(1H,3H)-dione and has been demonstrated to be susceptible. In general, a dose of from about 300 mg./kg./day to about 3200 mg./kg./day embraces the effective range and can be used for the systemic treatment of susceptible DNA viral infections in humans and animals. More specifically, a dose of from about 300 mg./kg.day to about 1600 mg./kg.day can be used for the systemic treatment of infections due to herpes simplex type 1 virus. The dose can be administered once per day or in increments throughout the day in order that an antiviral concentration of compound is present in the blood for a minimum of at least 8 hours of the day. For example, a range of about $1 \times 10^{-4}$M to about $4 \times 10^{-4}$M of 1-(2-deoxy-β-D-ribofuranosyl)-5-ethyl-5,6-dihydro-s-triazine-2,4-(1H,3H)-dione in the blood can be used to treat infections due to herpes simplex type 1 virus. The blood levels can be determined after administration of a suitable radiolabeled form of the compound and determining the level of the compound at appropriate times after compound administration. A method useful for such determinations is that described by G. L. Neil et al., published in Biochemical Pharmacology, 20, 3295-3308 (1971).

A group of compounds within the scope of formula 1a are those wherein X and Z are oxygen.

One group of compounds within the scope of formula 1a are those wherein X is imino and Z is oxygen.

Another group of compounds within the scope of formula 1a are those wherein X is oxygen and Z is sulfur.

One group of compounds within the scope of formula 1a are those of formula 1a-1.

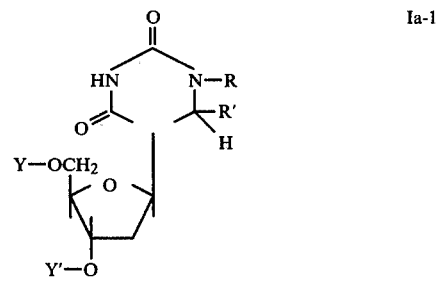

Ia-1 wherein R is selected from the group consisting of hydrogen, lower alkyl of 2 through 4 carbon atoms, cyclopropyl; R' is selected from the group consisting of hydrogen and lower alkyl of 1 through 4 carbon atoms; Y is selected from the group consisting of hydrogen, carboxacyl of from 1 through 18 carbon atoms, and phosphono; and Y' is selected from the group consisting of carboxacyl of from 1 through 18 carbon atoms and hydrogen.

Another group of compounds within the scope of formula 1a-1 are those wherein R is selected from the group consisting of hydrogen, ethyl, n-propyl, isopropyl and cyclopropyl.

A group of compounds within the scope of formula 1a-1 are those wherein R' is hydrogen.

A group of compounds wherein the scope of formula 1a-1 are those wherein Y and Y' are hydrogen.

A group of compounds within the scope of formula 1a-1 are those wherein Y, Y' and R' are hydrogen.

Another group of compounds within the scope of formula 1a-1 are those wherein Y and Y' are carboxacyl of from 1 through 18 carbon atoms and R' is hydrogen.

Another group of compounds within the scope of formula 1a-1 are those wherein Y is carboxacyl of from 1 through 18 carbon atoms; Y' and R' are hydrogen.

Still another group of compounds within the scope of formula 1a-1 are those wherein Y' is carboxacyl of from 1 through 18 carbon atoms; and Y and R' are hydrogen.

A group of compounds within the scope of formula 1a are those of formula 1a-2.

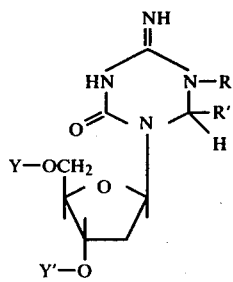

Wherein R is selected from the group consisting of hydrogen, lower alkyl of 1 through 4 carbon atoms and cyclopropyl; R' is selected from the group consisting of hydrogen and lower alkyl of 1 through 4 carbon atoms; Y is selected from the group consisting of hydrogen, carboxacyl of from 1 through 18 carbon atoms, and phosphono; Y' is selected from the group consisting of carboxacyl of from 1 through 18 carbon atoms and hydrogen; and pharmaceutically acceptable salts thereof.

A group of compounds within the scope of formula 1a-2 are those wherein R' is hydrogen.

Another group of compounds within the scope of formula 1a-2 are those wherein Y and Y' are hydrogen.

One group of compounds within the scope of formula 1a-2 are those wherein Y, Y' and R' are hydrogen.

Another group of compounds within the scope of formula 1a-2 are those wherein Y and Y' are carboxacyl of from 1 through 18 carbon atoms; and R' is hydrogen.

Another group of compounds within the scope of formula 1a-2 are those wherein Y is carboxacyl of from 1 through 18 carbon atoms; and Y' and R' are hydrogen.

Still another group of compounds within the scope of formula 1a-2 are those wherein Y' is carboxacyl of from 1 through 18 carbon atoms; and Y and R' are hydrogen.

Another group of compounds within the scope of formula 1a are those of formula 1a-3.

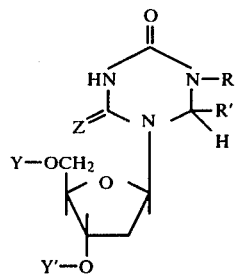

wherein R is selected from the group consisting of hydrogen, lower alkyl of 1 through 4 carbon atoms, and cyclopropl; R' is selected from the group consisting of hydrogen and lower alkyl of 1 through 4 carbon atoms; Y is selected from the group consisting of hydrogen, carboxacyl of from 1 through 18 carbon atoms, and phosphono; Y' is selected from the group consisting of carboxacyl of from 1 through 18 carbon atoms and hydrogen.

A group of compounds within the scope of formula 1a-3 are those wherein R' is hydrogen.

One group of compounds within the scope of formula 1a-3 are those wherein Y and Y' are hydrogen.

One group of compounds within the scope of formula 1a-3 are those wherein Y, Y' and R' are hydrogen.

Another group of compounds within the scope of formula 1a-3 are those wherein Y and Y' are carboxacyl of from 1 through 18 carbon atoms and R' is hydrogen.

Another group of compounds within the scope of formula 1a-3 are those wherein Y is carboxacyl of from 1 through 18 carbon atoms, Y' and R' are hydrogen.

Still another group of compounds within the scope of formula 1a-3 are those wherein Y' is carboxacyl of from 1 through 18 carbon atoms, Y and R' are hydrogen.

Another group of compounds within the scope of formula 1a are those of formula 1a-4.

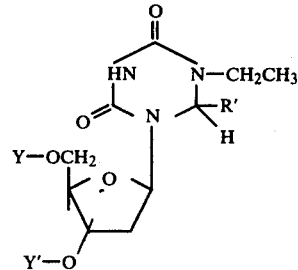

wherein R' is selected from the group consisting of hydrogen and lower alkyl of 1 through 4 carbon atoms; Y is selected from the group consisting of hydrogen, carboxacyl of from 1 through 18 carbon atoms, and phosphono; and Y' is selected from the group consisting of carboxacyl of from 1 through 18 carbon atoms and hydrogen.

A group of compounds within the scope of formula 1a-4 are those wherein R' is hydrogen.

One group of compounds within the scope of formula 1a-4 are those wherein Y and Y' are hydrogen.

Another group of compounds within the scope of formula 1a-4 are those wherein Y, Y' and R' are hydrogen.

Another group of compounds within the scope of formula 1a-4 are those wherein Y and Y' are carboxacyl of from 1 through 18 carbon atoms and R' is hydrogen.

Another group of compounds within the scope of formula 1a-4 are those wherein Y is carboxacyl of from 1 through 18 carbon atoms; and Y' and R' are hydrogen.

Still another group of compounds within the scope of formula 1a-4 are those wherein Y' is carboxacyl of from 1 through 18 carbon atoms; Y and R' are hydrogen.

For reason of brevity, compounds wherein Y'—O is in the threo configuration are not rendered in the same manner as compounds within the scope of formula 1a-1, 1a-2, 1a-3 and 1a-4, but the same illustrative scoping is intended.

In accordance with the process of this invention 5,6-dihydro-5R-6R'-s-triazines of the formula:

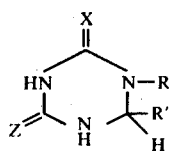

wherein R is selected from the group consisting of hydrogen, lower alkyl, phenyl, benzyl, cyclopropyl, lower-alkoxy lower-alkyl and lower-alkylthiolower-alkyl; R' is selected from the group consisting of hydrogen and lower alkyl; X is selected from the group consisting of oxygen, imino, lower-aklkylimino and lower acylimino; and Z is selected from the group consisting of oxygen and sulful; are mono- or disilylated by reaction with a trialkylsilyl halide, a trialkylsilylacetamide, a trimethylsilylamine, or hexamethyldisilazane, to form the corresponding mono-silyl compounds of formula A or the corresponding di-silyl compounds of formula B, respectively:

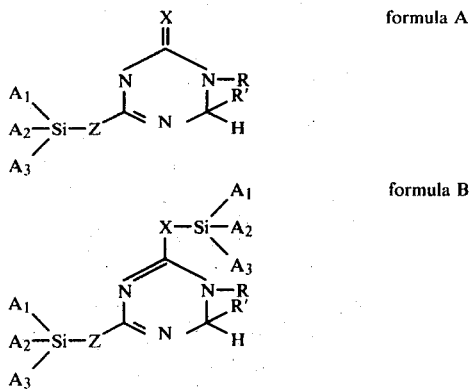

wherein R, R', X and Z have the above indicated meanings, and A$_1$, A$_2$, and A$_3$ represent lower alkyl groups of 1 to 4 carbon atoms.

A novel step of the process described, comprises reacting a mono-silyl compound of formula A with a 2-deoxy-3,5-blocked-D-pentofuransyl halide in the presence of a Lewis acid at an initial temperature of about minus (—) 25° C., with subsequent warming to about 25° C.

A disilyl compound of formula B can also be reacted with a 2-deoxy-3,5-blocked-D-pentofuranosyl halide in the presence of a Lewis acid at an initial temperature of about minus (—) 25° C. with subsequent warming to about 25° C. When the trialkylsilyl halide is used, an acid acceptor of the kind already indicated is included in the reaction mixture comprising a suitable reaction medium as is known in the art; see *Silylation of Organic Compounds*, Pierce Chemical Co., Rockford, Illinois (1968) and Chem. Pharm. Bull. 12 p. 352 (1964). In the practice of this invention, pyridine was successfully employed. The silylated 5,6-dihydro-s-triazine bases are recovered for further reaction with the blocked pentofuranosyl halides by conventional methods as described by the examples herein.

The sugar and the silylated base are reacted in the presence of a Lewis acid such as stannic halide, e.g., stannic chloride or bromide, and a solvent medium such as benzene, ethylene dichloride, toluene, chloroform, acetonitrile (preferred), nitromethane, dioxane and tetrahydrofuran. Mercuric bromide (preferably mixed with an equal weight of a molecular sieve, Linde Type 3A or 4A) or silver perchlorate can also be used as catalyst. The initial reaction is effected at temperatures around minus (—) 25° C. Later, the reaction temperature is increased to about 25° C. as described.

The "blocked" 2-deoxypentofuranosyl halide reactants include especially the bromo- and chloro-halides with blocking groups, i.e., a carboxacyl protective group as commonly used in sugar chemistry. Ordinarily, the blocking groups will be acetyl, toluoyl or benzoyl, but can be any equivalent protective carboxacyl group. The method of preparing the blocked sugar halide reactants is conventional, e.g., reacting the sugar with an alcohol in the presence of acid, protecting the free OH-groups with a suitable blocking group and forming the sugar halide by treatment with anhydrous, hydrogen halide in an organic solvent. The function of the blocking group is to protect the hydroxyl groups during the reaction.

Illustrative sugar halides are 1-(2-deoxy-3,5-di-O-toluoyl-D-ribofuranosyl)-chloride and 1-(2-deoxy-3,5-di-O-toluoyl-D-xylofuranosyl)-chloride.

The intermediate 1-(2-deoxy-3,5-di-O-acyl-$\beta$-D-ribofuranosyl)-5,6-dihydro-5R-6R'-s-triazines are recovered by conventional techniques such as solvent extraction, precipitation, filtration, crystallization and chromatography. The blocking groups are removed as described in order to obtain the object compounds 1-(2-deoxy-$\beta$-D-pentofuranosyl)-5,6-dihydro-5(R)-6R'-s-triazines.

The free nucleosides of the invention, compounds according to formula 1a wherein Y and Y' are hydrogen, can be acylated by standard procedures utilizing an acid halide or anhydride of an appropriate carboxylic acid including, for example, acetic anhydride, acetyl chloride, palmityl chloride, benzoyl chloride and succinic anhydride.

Various acylates of the free nucleosides of the invention can be made, and these acylates are useful to upgrade the free nucleosides. By following the procedure of Example 1, Part B, the 3',5'-di-esters are formed.

The 5'-mono-esters can be formed by standard procedures using a minimum amount of acylating agent, see, e.g. Example 6, Part B.

The 3'-mono-esters can be formed by tritylating the free nucleoside to give the 5'-trityl derivative, acylating with the acid halide or anhydride of the appropriate carboxylic acid such as disclosed in U.S. Pat. No. 3,426,012, Columns 5 and 6, to give the 3'-mono-ester 5'-trityl derivative, which then can be converted to the 3'-mono-ester by removal of the trityl group.

Phosphorylation is readily accomplished by the method described by D. Mitsunoku, K. Kato, and J. Kimura in Jour. Am. Chem. Soc. 91, p. 6510 (1969). After removal of the 3'-O-acyl group there are obtained 5'-phosphates according to the invention that have the desired anti-viral activity.

A preferred method of acylating the 3'-position is to first form an ether at the 5'-position with tert-butyldimethylsilyl chloride as described in Example 6, Part A. Acylation at the 3'-position is then accomplished as described in Example 6, Part B to obtain, e.g., 1-(5-O-tert-butyldimethylsilyl-3-O-lauroyl-2-deoxy-D-ribofuranosyl)-5-methyl-5,6-dihydro-s-triazine-2,4(1H,3H)-dione which is desilylated with tetra-n-butyl ammonium fluoride in tetrahydrofuran as in Example 6, Part C.

Preparation 1

Synthesis of new precursor
5-ethyl-5,6-dihydros-triazine-2,4-(1H,3H)-dione

Part A

Ethylbiuret

To a quantity [1.0 kg. (7.56 mole)] of ethyl allophanate is added 2.3 liter of 70 percent aqueous ethylamine. The reaction vessel is flushed with nitrogen gas in order to remove the oxygen present, and the reaction mixture is heated at temperatures in the range of 35° to 49° C. for 23 hours. The solution obtained is concentrated by removing much of the water and excess ethylamine by evaporation under reduced pressure and 45° C. A slurry results, which is cooled to 5° C. and filtered. The filter cake obtained is washed with 200 ml. of ice-cold, absolute ethanol. The washed crystals are dried under reduced pressure at 60° C. to give 802 gm. of ethylbiuret and starting ethyl allophanate. The 802 gm. quantity is again reacted with 2250 ml. of the 70 percent aqueous ethylamine diluted with an equal volume of water (2250 ml.). This reaction mixture is heated with stirring at 60° C. for 18 hours under a nitrogen atmosphere, and again much of the water and ethylamine is removed by evaporation under reduced pressure. The final volume is 1800 ml. The slurry thus obtained is cooled to 5° C. and filtered. After washing the white filter cake with ice-water and drying under reduced pressure at 50° C., there is obtained 597 gm. (62.69 percent yield) of the desired ethylbiuret having a melting point of 158.5° to 160° C.

Part B

1-Ethyl-5-azauracil

The ethylbiuret prepared in Part A, above, [592 gm. 4.7 mole] is dispersed in 24 liter absolute ethanol and 1.6 liter benzene. This reaction mixture is heated to the reflux temperature and 3.5 liter of solvent medium is removed by distillation. The solution is cooled to 60° C. and 2090 gm. of a 25 percent solution of sodium methoxide in methanol is slowly added over an interval of five minutes. That addition is followed by the addition of 820 gm. of ethylformate. This reaction mixture is heated at the reflux temperature for three (3) hours, whereupon the solution is cooled to 38° C. and concentrated hydrochloric acid is added slowly until the pH of the solution is 2. To the acidified solution is added more (3.4 liter) benzene. Then 2 liter of the solvent medium is removed by distillation under reduced pressure and 50° C. The mixture is then heated to 75° C. and filtered in order to remove the sodium chloride produced by the reaction. The filter cake of salt is washed with hot absolute ethanol which washings are added to the filtrate. The volume of the combined filtrate and absolute ethanol washings is reduced to 5 liter by evaporation under reduced pressure at 50° C. The resulting concentrate is cooled at 5° C. for 18 hours while crystals form. The crystals are collected on a filter and washed with cold (5°) ethanol. The washed crystals are dried in an oven under reduced pressure at 50° C. for 18 hours. There is thus obtained 408 gm. of crude product having a melting point at 137° to 139° C. A further purification is achieved by dissolving the 408 gm. in 4 liter methanol at reflux temperature. This solution is concentrated by allowing the methanol to evaporate to a volume of 2 l. while being heated on a steam bath. The concentrated solution is allowed to cool slowly to 25° C. It is then chilled to 5° C. for two hours. The crystals that form are collected on a filter and the filter cake is washed with ice-cold methanol. After drying there is obtained 389 gm. (58.7 percent yield) of 1-ethyl-5-azauracil having a melting point of 141° to 142° C. A second crop of crystals is recovered from the mother liquor after further concentration and cooling.

An analytical sample is prepared by recrystallizing from tetrahydrofuran. A 1.0 gm. sample is dissolved in 50 ml. and filtered while hot. The filtrate is concentrated to a volume of 25 ml. by evaporation of solvent medium and 50 ml. toluene is added. This solution is again concentrated to a volume of 25 ml. by evaporating the solvents on a steam bath. This concentrate is cooled to 25° C. and crystals formed. The crystals are collected on a filter, the filter cake is rinsed with Skellysolve B ®, essentially n-hexane, B.P. 60° C.–68° C., Skellysolve Oil Co., Inc. After drying the crystals in air, there are obtained 0.8 gm. of pure 1-ethyl-5-azauracil having a melting point of 144° C. to 145° C.

Analysis: Calc'd for $C_5H_7N_3O_2$: C, 42.55; H, 5.00; N, 29.78. Found: C, 42.33; H, 5.08; N, 29.36.

PART C

The desired precursor, 5-Ethyl-5,6-dihydro-s-triazine-2,4-(1H,3H)-dione.

To a quantity [370 gm., 2.62 mole] of the 1-ethyl-5-azauracil prepared in Part B, above is added 2200 ml. water and 40 gm. of 5 percent rhodium on activated charcoal. This mixture is put in a Parr hydrogenation chamber and hydrogen gas is introduced to a pressure of 50 pounds per square inch (p.s.i.) and the reaction system is heated to 100° C. When uptake of hydrogen ceases, the hydrogen pressure is increased to 200 p.s.i. and held there for 18 hours. The hydrogenated reaction is rinsed out of the reaction chamber with hot water, filtered while hot, and the filter is washed with one liter of water at 80° C. The aqueous solution is set aside at 25° C. for 18 hours, during which interval crystals form. The crystals are collected on a filter and dried at 50° C. under reduced pressure. There is thus obtained 70 gm. of 5-ethyl-5,6-dihydro-s-triazine-2,4-(1H,3H)-dione having a melting range between 220° C. and 224° C.

The mother liquor is concentrated by evaporating water until a slurry is obtained and the volume is 500 ml. After cooling, the crystals are collected on a filter and dried at 70° C. under reduced pressure. There is thus obtained 159 gm. of a second crop. These crystals are dissolved in 4.5 liter of methanol which has been heated to boiling. This methanolic solution is chilled to 5° C., set aside for 18 hours at that temperature, and then filtered. The filter cake is washed with 300 ml. of ice-cold methanol and dried at 50° C. under reduced pressure. There is thus obtained 77 gm. of product having a melting range between 220° C. and 224° C.

The filtrate is concentrated to a one liter volume by evaporating methanol. There is thus obtained 15.46 gm. of product which has a melting range between 211° C. and 218° C. After combining the 70 gm., 77 gm., and 15 gm. crops by dissolving them in 4 liter of boiling methanol, there is obtained, after chilling, an analytical sample weighing 138 gm. which has a melting range between 221° C. and 225° C.

Analysis: Calc'd for $C_5H_9N_3O_2$: C, 41.95; H, 6.34; N, 29.36. Found: C, 41.89; H, 6.55; N, 29.31.

Preparation 2

Synthesis of known precursor 5,6-dihydro-5-methyl-s-triazine-2,4-(1H,3H)-dione

Part A

Methylbiuret

A reaction mixture consisting of 200 gm. (1.5 mole) ethyl allophanate and 800 ml. of 40 percent aqueous methylamine is introduced into a two liter flask and the flask is loosely stoppered. After stirring for from 3 to 5 hours a clear solution is obtained. Stirring is continued for a total of 18 hours. The reaction medium is then allowed to evaporate until the odor of methylamine is no longer noticeable. The aqueous slurry thus obtained is filtered and the aqueous filtrate is discarded. The white solid on the filter is recrystallized from ethanol which contained a small proportion of methanol. There is thus obtained 125 gm. (71 percent yield) of methylbiuret as white crystals having a melting point of 173° C. to 175° C.

Part B 1-methyl-5-azauracil

A reaction mixture consisting of 70.2 gm (0.6 mole) of the 1-methylbiuret prepared in Part A above, 3.5 liter absolute ethanol, and 200 ml. benzene is heated to the reflux temperature with stirring in a 5-liter, three-necked flask fitted with a reflux condenser, a stirrer, and thermometer. The top of the condenser is fitted with a nitrogen outlet, but no water is run through the condenser. After removing the nitrogen outlet, 200 ml. of the medium is allowed to distill through the condenser. The reaction mixture is then cooled to 60° C., before 28 gm. (1.2 mole) of sodium metal is added slowly over an interval of five (5) minutes. A white solid precipitates, but stirring is continued until all the sodium is dissolved. At this point, 104 gm. (1.4 mole) of ethyl formate is added in one portion and the reaction mixture is again heated to the reflux temperature (about 75° C.) and refluxed for three (3) hours. The reaction mixture is cooled to about 30° C. and hydrogen chloride gas is blown over the surface until an acid pH is attained. The reaction mixture is again heated at the reflux temperature for 15 minutes. The hot mixture is filtered through a diatomaceous earth filter and the filter is washed with hot ethanol. The filtrate and washings are concentrated to a volume of 200 to 300 ml. by removing medium by evaporation under reduced pressure. The concentrate is cooled to 5° C. and set aside at that temperature for several hours for crystallization. The crystals are collected on a filter and washed with cold ethanol. After drying the crystals under reduced pressure there is obtained 69 gm. (90% yield) of 1-methyl-5-azauracil having a melting range from 200° C. to 205° C. A sample recrystallized three times from ethanol has a melting point of 213° C. to 214° C.

Part C

The desired known pecursor, 5,6-dihydro-5-methyl-s-triazine-2,4-(1H,3H)-dione

A hydrogenation mixture consisting of 203.5 gm. (1.6 moles) of the 1-methyl-5-azauracil prepared in Part B, above, 7 teaspoons of Raney Nickel, and 8 liter ethanol in a five-gallon autoclave is subjected to 750 p.s.i. hydrogen pressure at 125° C. for an interval of 12 hours. The hydrogen is flushed out of the chamber with nitrogen gas and the reaction mixture is siphoned out of the chamber into a five-gallon carboy. The walls of the chamber are washed down with water and these washings are siphoned into the carboy. The carboy is then flushed with nitrogen (<20 p.s.i.) so as to force the medium through a filter stick onto a filter bed of Dicalite 4200 (diatomaceous earth). The solids are retained in the carboy substantially undisturbed. The medium is then sucked through the dicalite filter under reduced pressure until 1 inch of liquid remains. The solids retained in the bottom of the carboy are now mixed with two (2) liters water and 500 ml. Dicalite 4200 and this mixture is added to the filter cake. The filter cake is then washed with water. The filtrate and washings are combined and the water is removed to a volume of 1200 ml. by evaporation under reduced pressure, 20 mm mercury, and 50° C. temperature. The concentrate thus obtained is heated to 90° C., and 95% aqueous ethanol is added to a volume of two liters. Upon cooling, crystallization occurs. The crystals are collected on a filter and dried. There is thus obtained 120 gm. (59% yield) of 5,6-dihydro-5-methyl-s-triazine-2,4-(1H,3H)-dione having a melting point of 252° C. to 254° C.

Preparation 3

Synthesis of new precursor 5-n-butyl-5,6-dihydro-s-triazine-2,4-(1H,3H)-dione

Part A n-Butylbiuret

Following the procedure described in Preparation 2, Part A, above, but substituting n-butylamine for the methylamine, there is prepared 60 gm. (35% yield) of n-butylbiuret having a melting point of 129° to 131° C.

Analysis: Calc'd for $C_6H_{13}N_3O_2$: C, 45.27; H, 8.23; N, 26.40. Found: C, 45.27; H, 8.02; N, 26.48.

Part B 1-n-Butyl-5azauracil

Following the procedure described in Preparation 2, Part B, above, but substituting the n-butylbiuret prepared in Part A, above, for the methylbiuret, there is prepared 60 gm. (92% yield) of 1-n-butyl-5-azauracil.

Part C

The desired new precursor, 5-n-butyl-5,6-dihyro-s-triazine-2,4-(1H,3H)-dione

Following the procedure described in Preparation 2, Part C, above, but substituting the 1-n-butyl-5-azauracil prepared in Part B, above, for the 1-methyl-5-azauracil, there is prepared 40 gm. (67% yield) of the desired new precursor 5n-butyl-5,6-dihydro-s-triazine-2,4-(1H,3H)-dione having a melting point of 205° C. to 207° C.

Analysis:

Calc'd. for $C_7H_{13}N_3O_2$: C, 49.12; H, 7.65; N, 24.55. Found: C, 49.17; H, 7.68; N, 24.56.

Preparation 4

Synthesis of new precursor, 3,4,5,6-tetrahydro-4-imino-5-methyl-s-triazine-2-(1H)-one

Part A

New antecedent, 5,6-dihydro-5-methyl-4-thio-s-triazine-2-(1H,3H)-one 12.90 gm. of 5,6-dihydro-5-methyl-s-triazine-2,4-(1H,3H)-dione (prepared as in Preparation 2, Part C, above) is added to 500 ml. of pyridine. With protection from moisture, 33.0 ml. of Bistrimethylsilyltrifluoroacetamide is added and the reaction mixture is stirred at 25° C. for 18 hours. This reaction mixture is poured into 7.50 gm. phosphorus pentasulfide from which pyridine has been distilled (under vacuum) twice; heated at reflux, with stirring, for 42 hours. After first cooling to 25° C., the residue is evaporated under vacuum to dryness and tritrated with chloroform and the resulting solids washed with chloroform to yield 9.45 gm. of 5,6-dihydro-5-methyl-s-triazine-2,4-(1H,3H)-dione. The chloroform solution is evaporated to dryness and the resulting residue chromatographed on 1.4 kg. silica gel using 2% methanol and chloroform as eluent. Fractions are collected with rf. 0.7 (in 15% methanol/chloroform) to give 395 mg. of 5,6-dihydro-5-methyl-2-thio-s-triazine-2,4-(1H,3H)-dione and those fractions containing material with rf. 0.65 (15% methanol/chloroform) to yield 92 mg. of 5.6-dihydro-5-methyl-4-thio-s-triazine-2,4-(1H,3H)-dione, melting point 273°–274° C.

Analysis: Calc'd. for $C_4N_7N_3OS$: (145.18): C, 33.09; H, 4,86; N, 28.94; S, 22.08. Found: C, 33.01; H, 5.20; N, 29.18; S, 21.67.

Following the same procedure, but substituting
;b 5,6-dihydro-s-triazine-2,4-(1H,3H)-dione,
5,6-dihydro-5-ethyl-s-triazine-2,4-(1H,3H)-dione,
5,6-dihydro-5-n-propyl-s-triazine-2,4-(1H,3H)-dione,
5,6-dihydro-5-cyclopropyl-s-triazine-2,4-(1H,3H)-dione,
5,6-dihydro-5-isopropyl-s-triazine-2,4-(1H,3H)-dione,
5,6-dihydro-5-methoxymethyl-s-triazine-2,4-(1H,3H)-dione, and
5,6-dihydro-5-methylthiomethyl-s-triazine-2,4-(1H,3H)-dione, for the 5,6-dihydro-5-methyl-s-triazine-2,4(1H,3H)-dione, there are prepared the corresponding
5,6-dihydro-4-thio-s-triazine-2-(1H,3H)-one,
5,6-dihydro-5-ethyl-4-thio-s-triazine-2-(1H,3H)-one,
5,6-dihydro-5-n-propyl-4-thio-s-triazine-2-(1H,3H)-one,
5,6-dihydro-5-cyclopropyl-4-thio-s-triazine-2-(1H,3H)-one,
5,6-dihydro-5-isopropyl-4-thio-s-triazine-2-(1;H,3H)-one,
5,6-dihydro-5-methoxymethyl-4-thio-s-triazine-2-(1H,3H)-one, and
5,6-dihydro-5-methylthiomethyl-4-thio-s-triazine-2-(1H,3H)-one, respectively.

Part B

New precursor, 3,4,5,6-tetrahydro-4-imino-5-methyl-s-triazine-2-(1H)-one

A cold reaction mixture is prepared by mixing 0.725 gm. (0.005 mole) of the 5,6-dihydro-5-methyl-4-thio-s-triazine-2-(1H,3H)-one prepared as in Part A, above, and 25 ml. of a saturated methanolic solution of ammonia which has been cooled to 0° C. The reaction mixture is put in a stainless steel pressure chamber and heated at 105° C. for 72 hours. After cooling and filtering, the filter cake is washed with ice-cold methanol and dried under reduced pressure at 50° C. and the product collected. The filtrate and methanol washings are combined and the methanol is removed by evaporation. The residue thus obtained is triturated with 5 ml. methanol at 25° C. to give additional product. Both crops of product are combined and dissolved in 20 ml. of boiling ethanol, water being added until solution is complete. The aqueous ethanol solution is then cooled to 5° C. and refrigerated at that temperature for 18 hours. The crystals that are formed are collected on a filter and washed with cold ethanol at 5° C. The washed crystals are dried under reduced pressure at 50° C. to give 3,4,5,6-tetrahydro-4-imino-5-methyl-s-triazine-2-(1H)-one.

Following the procedure of Preparation 4, Part B, but substituting
5,6-dihydro-4-thio-s-triazine-2-(1H,3H)-one,
5,6-dihydro-5-ethyl-4-thio-s-triazine-2-(1H,3H)-one,
5,6-dihydro-5-n-propyl-4-thio-s-triazine-2-(1H,3H)-one,
5,6-dihydro-5-cyclopropyl-4-thio-s-triazine-2-(1H,3H)-one,
5,6-dihydro-5-isopropyl-4-thio-s-triazine-2-(1H,3H)-one,
5,6-dihydro-5-methoxymethyl-4-thio-s-triazine-2-(1H,3H)-one, and
5,6-dihydro-5-methylthiomethyl-4-thio-s-triazine-2-(1H,3H)-one for the 5,6-dihydro-5-methyl-4-thio-s-triazine-2-(1H,3H)-one, there are prepared the corresponding
3,4,5,6-tetrahydro-4-imino-s-triazine-2-(1H)-one,
3,4,5,6-tetrahydro-4-imino-5-ethyl-s-triazine-2-(1H)-one,
3,4,5,6-tetrahydro-4-imino-5-n-propyl-s-triazine-2-(1H)-one,
3,4,5,6-tetrahydro-4-imino-5-cyclopropyl-s-triazine-2-(1H)-one,
3,4,5,6-tetrahydro-5-isopropyl-4-imino-s-triazone-2-(1H)-one,
3,4,5,6-tetrahydro-5-methoxymethyl-4-imino-s-triazine-2-(1H)-one, and
3,4,5,6-tetrahydro-5-methylthiomethyl-4-imino-s-triazine-s-(1H)-one, respectively.

Preparation 5

Preparation of 4-imino-4-N-acetyl-3,4,5,6-tetrahydro-5-methyl-s-triazine-2-(1H)-one To 1.28 gm. 10 mm. of 4-imino-5,6-dihydro-5-methyl-s-triazine-2(1H,3H)-one is added 50 ml. of pyridine, followed by 10 ml. of acetyl chloride at 25° C. for 18 hours. The reaction mixture is evaporated to dryness and is the desired 4-imino-N-acetyl-3,4,5,6-tetrahydro-5-methyl-5-triazine-2-(1H)- is isolated by crystallization from methanol.

Preparation 6

Synthesis of precursor, 2-deoxy-3,5-di-O-toluoyl-D-ribofuranosyl chloride

A reaction mixture consisting of 20 gm. (0.15 mole) 2-deoxy-D-ribose, 360 ml. methanol, and 20.0 ml. of a 1% solution of hydrogen chloride in methanol is stirred for one hour at 25° C. Pyridine is added to a slight excess, and the volatile components are then removed by evaporation under reduced pressure. The residue is dissolved in pyridine and the pyridine is evaporated under vacuum. The residue is dissolved in 125 ml. pyridine and the solution is cooled to 0° C. While maintaining the temperature at 0° C. to 10° C., 50.0 gm. (0.33 mole) p-toluoyl chloride is added. Afterwards, the reaction mixture is allowed to gradually warm to 25° C. while stirring is continued for about 16 hours. After this prolonged interval of stirring, the reaction mixture is again cooled to 0° C. and 400 ml. water is added followed by 200 ml. chloroform. The addition of the water decomposed the excess p-tolyoyl chloride. During addition the temperature is not permitted to rise above 10° C. The mixture is stirred for one hour, the organic and aqueous phases are allowed to separate, and the aqueous phase is recovered for purposes of extration with two-150 ml. portions of chloroform. The combined original chloroform layer and chloroform extracts is washed with three-100 ml. portions of 3N sulfuric acid at 5° C., three-100 ml. portions of saturated aqueous sodium bicarbonate, and one 200 ml. portion of water. The washed chloroform solution is dried with anhydrous magnesium sulfate, and after removing the magnesium sulfate by filtration, the chloroform is removed by evaporation under reduced pressure. There is thus obtained 59.5 gm. of 1-methoxy-3,5-di-O-toluoyl-2-deoxy-D-ribose as a dark amber gum. To 73.5 gm. of 1-methoxy-3,5-di-O-toluoyl-2-deoxy-D-ribose is added 175 ml. diethyl ether and this ether solution is poured into 365 ml. of glacial acetic acid that has been saturated at 17° C. with anhydrous hydrogen chloride gas. The addition is optimally made at 0° C. to 5° C. With vigorous stirring at 0° C., additional hydrogen chloride gas is introduced until crystals form. Stirring is continued for 3 to 5 minutes before filtering. The filter cake is washed thoroughly with diethyl ether, and the washed crystals are dried under reduced pressure at 25° C. There is thus obtained 48 gm. (66% yield) of 1-chloro-3,5-di-O-toluoyl-2-deoxy-D-ribose.

The crude title compound is purified by dissolving the above product in boiling carbon tetrachloride, chilling the solution immediately to minus (−) 10° C. and then setting it aside at 5° C. to 10° C. for 2 hours. The crystals of 1-chloro-3,5-di-O-toluoyl-2-deoxy-D-ribose are recovered on a filter.

EXAMPLE 1

Preparation of
1-(2-deoxy-β-D-ribofuranosyl)-5-ethyl-5,6-dihydro-s-triazine-2,4-(1H,3H)-dione Part A Synthesis of the monosilylated precursor 5-ethyl-5,6-dihydro-2-O-(trimethylsilyl)-s-triazine-4-(3H)-one.

A reaction mixture consisting of 7.15 gm. (0.05 mole) of 5-ethyl-5,6-dihydro-s-triazine-2,4-(1H,3H)-dione prepared in Preparation 1, Part C, (above), 150 ml. hexamethyldisilazane, and a catalytic amount (3mg.) of ammonium sulfate is heated at the reflux temperature for 48 hours. The volatiles are removed by evaporation under reduced pressure, and the residue thus obtained is held under reduced pressure for 18 hours. The 5-ethyl-5,6-dihydro-2O-(trimethylsilyl)-s-triazine-4-(3H)-one is obtained as a white solid that gave an NMR spectrum in deuterated chlorform (CDCl$_3$): NH at 7.9 δ and a ring CH$_2$ at 4.33 δ (S).

Part B

Preparation of intermediates 1-(3,5-di-O-toluoyl-2-deoxy-(β-D-ribofuranosyl)-5-ethyl-5,6-dihydro-s-triazine-2,4-(1H,3H)-dione and 1-(3,5-di-O-toluoyl-2-deoxy-α-D-ribofuranosyl)-5-ethyl-5,6-dihydro-s-triazine.

A solution consisting of the 2-O-trimethylsilyl ether of 5-ethyl-5,6-dihydro-s-triazine-2,4-(1H,3H)-dione prepared in Part A above, and 625 ml. of reagent grade acetonitrile is chilled, in a reaction vessel freed of moisture and oxygen by flushing with nitrogen, to a temperature of minus (−) 25° C., before 3.75 ml. of fuming, anhydrous stannic chloride is injected. This reaction mixture is stirred for five (5) minutes at the minus (−)25° C. temperature whereupon 10.0 gm. (0.025mole of 3,5-di-O--toluoyl-2-deoxy-D-ribofuranosyl chloride that has been dissolved in 20 ml. ethylene dichloride is injected. This reaction mixture is stirred at the minus (−) 25° C. for 5 minutes before transferring the reaction vessel to a hot water bath where the reaction mixture is warmed to 20° C. Stirring is continued at the 20° C. temperature for 35 minutes when 100 ml. of saturated aqueous sodium bicarbonate is added. There is then added enough chloroform to bring the total volume to 400 ml. The organic phase is recovered and washed once with saturated aqueous sodium bicarbonate and once with water. It is dried by adding anhydrous magnesium sulfate. The dried organic solution is filtered to remove the magnesium sulfate and the filter is rinsed with 200 ml. chloroform. The chloroform is then removed by evaporation under reduced pressure to give 10.0 gm. of a foam. The foam is dissolved in 30 ml. chloroform and the solution is chromatographed over a series of three prepacked silica gel columns. (E. Merck, Silica gel 60 pre-packed column for liquid chromatography, size C.). The columns are developed with a mixture of cyclohexane and acetone in proportions 2.5 to 1. The flow rate is 2 ml./min. and 20 ml. fractions are collected. The eluate in fractions 135 through 180 is recovered by combining the fractions and removing the solvents by evaporation. The product weighs 3.15 gm. An analytical sample is obtained by recrystallization from a mixture of acetone and Skellysolve B®(1:1v/v). The product, 1-(3,5-di-0-toluyl-2-deoxy-β-D-ribofuranosyl)5-ethyl-5,6-dihydro-s-triazine-2,4-(1H,3H)-dione, has a melting point of 166.5° C. to 168° C.

Analysis: Calc'd for C$_{26}$H$_{29}$N$_3$O$_4$: C, 63.02; H, 5.90; N, 8.48. Found C, 62.89; H, 5.88; N, 8.24.

$[α]_D^{25} = -47°$ (c=0.885 in chloroform).

The eluate in fractions 191 through 246 is similarly recovered by combining the fractions and removing the solvents by evaporation. The product weights 2.60 gm. An analytical sample is prepared by recrystallization from a mixture of acetone and Skellysolve B® (1:1 v/v). There is thus obtained pure 1-(3,5-di-0-toluoyl-2-deoxy-α-D-ribofuranosyl-5-ethyl-5,6-dihydro-s-triazine-2,4-(1H,3H)-dione having a melting point of 134.5° C. to 136° C.

Analysis: Calc'd for C$_{26}$H$_{29}$N$_3$O$_4$: C, 63.02; H, 5.90; N, 8.48. Found: C, 63.29; H, 5.93; N, 8.37.

$[α]_D^{25} = 0°$ (c =0.8935 in chloroform).

Part C

Preparation of desired compound 1-(2-deoxy-β-ribofuranosyl)-5-ethyl-5,6-dihydro-s-triazine-2,4(1H,3H)-dione A reaction mixture is obtained by adding 0.33 ml. of a 25% solution of sodium methoxide in methanol to a solution consisting of 3.2 gm. (0.065 mole) of 1-(3,5-di-0-toluoyl-2-deoxy-β-D-ribofuranosyl)-5-ethyl-5,6-dihydro-s-triazine-2,4-(1H,3H)-dione (prepared in Part A, above) and 65 ml. methanol.

The mixture was stirred for 18 hours. A few chips of solid carbon dioxide are added and the methanol is removed by evaporation under reduced pressure. The residue thus obtained is dispersed in a mixture of chloroform and water (20 ml. and 100 ml., respectively) and the aqueous phase is allowed to separate and is recovered. It is washed with four-20 ml. portions of chloroform and filtered. The water is removed from filtrate by evaporation under reduced pressure. The solid thus obtrained in recrystallized from absolute ethanol to give 1.11 gm. of 1-(2-deoxy-$\beta$-D-ribofuranosyl)-5-ethyl-5,6-dihydro-s-triazine-2,4-(1H,3H)-dione having a melting point of 161.5° to 162.5° C.

Analysis:
Calc'd for $C_{10}H_{17}N_3O_5$: C, 46.32; H, 6.61; N, 16.21. Found: C, 46.43; H, 6.74; N, 15.68.

$[\alpha]_D^{25} = -7°$ (c=0.987 in water)

NMR $D_2O$ gave $H_1'$, 3 line pattern at 6.19 $\delta$, and ring $CH_2$, 4.72 $\delta$, singlet.

EXAMPLE 2

Preparation of 1-(2-deoxy-$\beta$-D-ribofuranosyl)-5,6-dihydro-5-methyl-s-triazine-2,4-(1H,3H)-dione and 3'5'-di-O-toluate thereof.

Part A

Activated precursor 2,4-bis(trimethylsilyloxy)-5,6-dihydro-5-methyl-s-triazine.

A reaction mixture consisting of 1.3 gm. (0.010 mole) 5,6-dihydro-5-methyl-s-triazine-2,4(1H,3H)-dione in 25 ml. pyridine and 6 ml. of bis-trimethylsilyltrifluoroacetamide containing 1% trimethylsilyl chloride is warmed to 50° C. and stirred for 16 hrs. The mixture is then cooled to 25° C., and the pyridine medium along with other volatile components are removed by evaporation under reduced pressure at 60° C. The residue thus obtained is purified by distilling added toluene under reduced pressure. The toluene distillation is repeated, and any traces of toluene are removed by holding the residue under reduced pressure for 16 hrs. at 25° C. There is thus obtained a quantity (about 80% yield) of 2,4-bis-(trimethylsilyloxy)-5,6-dihydro-5-methyl-s-triazine.

Part B

Alternative preparation of activated precursor 2,4-bis-(trimethylsilyloxy)-5,6-dihydro-5-methyl-s-triazine.

A reaction mixture consisting of 1.9 gm. (0.015 mole) of 5,6-dihydro-5-methyl-s-triazine-2,4-(1H,3H)-dione, 50 ml. hexamethyldisilazane, and 2 mg. ammonium sulfate is heated at the reflux temperature in an environment free from moisture for 48 hours. The mixture is then cooled to 25° C. and the excess hexamethyldisilazane is removed by evaporation under reduced pressure. Toluene is added to the residue thus obtained and anhydrous conditions are maintained by flushing with nitrogen gas. Toluene is removed by distillation. This toluene distillation is repeated; and the 2,4-bis(trimethylsilyloxy)-5,6-dihydro-5-methyl-s-triazine thus obtained is kept under high vacuum until used.

Part C

Synthesis of activated precursor 2-(trimethylsilyloxy)-5,6-dihydro-5-methyl-s-triazine-4-(3H)-one.

A reaction mixture consisting of 1.28 gm. (0.010 mole) 5,6-dihydro-5-methyl-s-triazine-2,4(1H,3H)-dione, 40 ml. pyridine, and 4.0 ml. bis-trimethylsilyltrifluoroacetamide is stirred continuously at 25° C. for 18 hours. The volatiles are then removed by evaporation under reduced pressure, and the residue thus obtained is freed of any pyridine by adding acetonitrile and distilling under reduced pressure. The distillation is repeated and there is thus obtained a quantitative yield of 2-(trimethylsilyloxy)-5,6-dihydro-5-methyl-s-triazine-4(3H)-one.

Part D

Preparation of intermediate 1-(2-deoxy-3,5-0-toluoyl-$\beta$-D-ribofuranosyl)-5,6-dihydro-5-methyl-s-triazine-2,4-(1H,3H)-dione. )

A solution consisting of 13.6 gm (0.05 mole) of the activated precursor 2,4-bis(trimethylsilyloxy)-5,6-dihydro-5-methyl-s-triazine prepared in Part A, above, and 625 ml. acetonitrile is chilled to minus (−)24° C. and 3.75 ml. of fuming anhydrous stannic chloride is added. This solution is stirred for five (5) minutes, in order to effect solution of the catalyst, before a room temperature (28° C.) solution consisting of 9.7 gm. (0.025 mole) of 2-deoxy-3,5-ditoluoyl-$\beta$-D-ribofuranosyl chloride and 100 ml. ethylene dichloride is added. This reaction mixture is stirred at minus (−20° C. for five (5) minutes before being warmed to 25° C. Stirring is continued as the solution gradually becomes a dark green color. After adding 100 ml. of saturated aqueous sodium bicarbonate, the mixture is stirred for one (1) hour, and chloroform is added until an aqueous phase begins to separate. The aqueous phase is allowed to separate, and the organic phase is recovered. The organic phase is washed once with saturated aqueous sodium bicarbonate and once with water. All traces of moisture are removed by drying over anhydrous magnesium sulfate. The dried solution is filtered, and the magnesium sulfate on the filter is washed well with chloroform. The filtrate and washings are combined and the organic solvents are removed by evaporation under reduced pressure followed by high vacuum. The foamy residue is dissolved in 50 ml. ethyl acetate, and, after seeding, is set aside at 5° C. for 48 hours. The crystallizing mixture is shaken periodically during the 48 hours. Th crystals are collected on a filter, washed well with ethyl acetate, and dried overnight under reduced pressure. There is thus obtained 3.46 gm. (28.8% yield) of the desired product. A pure sample is prepared by dissolving 2.0 gm. in 45 ml. hot ethyl acetate, filtering, concentrating the filtrate to one-third (⅓) its original volume, and crystallizing finally at minus (−)20° C. There is thus obtained 1.6 gm. (80% yield) of 1-(2-deoxy-3,5-di-0-toluoyl-$\beta$-D-ribofuranosyl)-5,6-dihydro-5-methyl-s-triazine-2,4-(1H,3-H)-dione having a melting point of 184° C. to 185° C.

Analysis: Calc'd for $C_{25}H_{27}N_3O_9$: C, 62.36; H, 5.65; N, 8.73. Found: C, 62.18; H, 5.69; N, 8.68.

U.V. $\lambda$end absorption, 241, 269, 281 nm($\epsilon$=31,800, 2,250, 1,300) ethanol I.R. NH: 3200 cm$^{-1}$; NH/CH: 3080; C=O: 1730, 1710; C=C/$\beta$NH: 1610, 1575, 1520; C—C/C—N: 1275, 1265, 1250, 1180, 1110, 1100; other: 755.

$[\alpha]_D - 46°$ (c=1.087 in chloroform)

NMR: $J_{1'-2'\alpha}$=9Hz;
$J_{1'-2'}$=6Hz.

Part E

Preparation of 1-(2-deoxy-3,5-di-O-toluoyl-(β-D-ribofuranosyl)-5,6-dihydro-5-methyl-s-triazine-2,4-(1H,3H)-dione from monosilyloxy precursor, 2-(trimethylsilyloxy)-5,6-dihydro-5-methyl-s-triazine-4-(3H)-one.

Following the procedure described in Part C, above, but doubling the amounts of reactants and reagents and substituting the 2-(trimethylsilyloxy)-5,6-dihydro-5-methyl-s-triazine-4-(3H)-one for 2,4-bis(trimethylsilyloxy)-5,6-dihydro-5-methyl-s-triazine there is prepared the corresponding desired intermediate 1-(2-deoxy-3,5-di-O-toluoyl-β-D-ribofuranosyl)-5,6-dihydro-5-methyl-s-triazine-2,4-(1H,3H)-dione weighing 3.8 gm. and having a melting point of 183° C. to 185° C.

Part F

Deacylation to obtain the object compound 1-(2-deoxy-β-D-ribofuranosyl)-5,6-dihydro-5-methyl-s-triazine-2,4-(1H,3H)-dione To a solution consisting of 7.85 gm. (0.016 mole) of 1-(2-deoxy-3,5-di-O-toluoyl-β-D-ribofuranosyl)-5,6-dihydro-5-methyl-s-triazine-2,4-(1H,3H)-dione (prepared in Parts C and D, above), and 160 ml. methanol, is added 0.8 ml. of a 25% solution of sodium methoxide in methanol. This reaction mixture is stirred for 18 hours when a few chips of solid carbon dioxide are added and stirring is continued for another 10 minutes. Forty gm. of silica gel are added and the methanol is removed by evaporation under reduced pressure. The residual white powder thus obtained is transferred to a column of silica gel and then the column is developed with a solution of 5% methanol in chloroform and fractions having positive $H_2SO_4$ char are combined. After removing the solvents by evaporation, a 1 gm. sample of the solid residue is dissolved in 4 ml. of hot methanol to which solution is added 24 ml. ethyl acetate. Crystallization occurs at 25° C., and there is thus obtained 0.79 gm. (79% recovery) of the compound having a melting point at 142° C. to 143° C.

Analysis: Calc'd for $C_9H_{15}N_3O_5$: C, 44.08; H, 6.17; N, 17.13. Found: C, 43.88; H, 6.18; N, 17.31.

Specific Rotation $[\alpha]_D^{25} = -6°$ (c=0.9168, water)

EXAMPLE 3

Preparation of 1-(2-deoxy-β-D-ribofuranosyl)-5-n-butyl-5,6-dihydro-s-triazine-2,4-(1H,3H)-dione and the di-O-toluate thereof.

Part A

Synthesis of the activated, monosilylated precursor 5-n-butyl- 5,6-dihydro-2-O-(trimethylsilyl)-s-triazine-4-(3H)-one.

A reaction mixture consisting of 860 mg. (0.005 mole) of 5-n-butyl-5,6-dihydro-s-triazine-2,4-(1H,3H)-dione (prepared in Preparation 3, above), 10 ml. pyridine, and 2.5 ml. of bistrimethylsilyltrifluoro-acetamide containing 1% trimethylsilylchloride are warmed to 50° C. and stirred for 18 hours. The mixture is then cooled to 25° C. and the volatile components are removed by evaporation under reduced pressure. The residue thus obtained is dispersed in toluene and the toluene is removed by distillation. This procedure is repeated three times. The residual solid thus obtained is stored under high vacuum until used. The $NMR_{CDCl_3}$ is consistent with monosilylation.

Part B

Preparation of intermediate, 1-(2-deoxy-3,5-di-D-toluoyl-β-D-ribofuranosyl)-5-n-butyl-5,6-dihydro-s-triazine,2,4-(1H,3H)-dione.

A quantity (12.17 gm., 0.005 mole) of 5-n-butyl-5,6-dihydro-2O-(trimethylsilyl)-s-triazine-4-(3H)-one is dispersed in 625 ml. acetonitrile and chilled to minus (−) 22° C. in a reaction vessel from which moisture and oxygen has been removed by flushing with nitrogen. To this chilled solution is added (by injection) 3.75 ml. of fuming, anhydrous stannic chloride. Stirring is continued for 10 minutes, and the reaction mixture becomes homogeneous. There is then added 9.8 gm. (0.025 mole) of the 1-(2-deoxy-3,5-di-O-toluoyl-D-ribofuranosyl)-chloride that has been dissolved in 100 ml. ethylene dichloride. After continued stirring at minus (−) 22° C. for 15 minutes, the reaction mixture is warmed to 22° C. in a hot water bath. The reaction mixture is held at 22° C. for 6.5 hours when 100 ml. saturated, aqueous sodium bicarbonate is added and the buffered solution is stirred for 30 minutes. Chloroform is then added in an amount sufficient to cause separation of the aqueous phase. The organic phase is removed and washed with 200 ml. water. The washed organic phase is dried over anhydrous sodium sulfate and the solvents are removed by evaporation under reduced pressure. The semisolid residue thus obtained is triturated with 75 ml. hot ethyl acetate and cooled to 25° C. The precipitate that forms weighs 3.6 gm. and it is shown to be starting material. The ethyl acetate filtrate is taken to dryness by evaporation and 15 gm. of semi-solid material is transferred to a 650 gm. column of silica gel. The column is developed with 4% methanol in chloroform and the fractions containing nucleoside eluates are saved and combined. The solvents are removed by evaporation under reduced pressure and the residue thus obtained is dissolved in 30 ml. acetone. Skellysolve B ® is added to the acetone solution until turbidity developed. Crystallization proceeded while the turbid mixture is held at 25° C. for 18 hours. There is thus obtained 4.9 gm. of white crystals in two crops. A portion of these crystals (4.1 gm.) is transferred to a series of three silica gel 60 columns [e. Merck prepacked columns type C] for medium pressure liquid chromatography with a solvent system of acetone and cyclohexane in proportions 1:2. The flow rate is 3 ml. per minute and 15 ml. fractions are collected. Fractions 124 through 152 are combined and the solvents are removed by evaporation under reduced pressure. The residue thus obtained is recrystallized from a mixture of acetone and Skellysolve B ® to give the desired 1-(2-deoxy-3,5-di-O-toluoyl-β-D-ribofuranosyl)-5-n-butyl-5,6-dihydro-s-triazine-2,4-(1H,3H)-dione, having a melting point of 170.5° to 172° C.

Analysis: Calc'd for $C_{28}H_{33}N_3O_7$: C, 64.23; H,6.35; N, 8.03. Found: C, 64.33; N, 6.28; N, 7.91.

$[\alpha]_D^{25} = -47°$ (c=0.995 in chloroform)

IR: NH: 3200 cm$^{-1}$; NH/=CH: 3060; C=O: 1725, 1710, 1695; C=C/other: 1610, 1575; 1510, 1490; C—O/C—N: 1280, 1250, 1175, 1100, 1085, 1025; other: 755.

Part C

Preparation of the object compound 1-(2-deoxy-β-D-ribofuranosyl)-5-n-butyl-5,6-dihydro-s-triazine-2,4-(1H,3H)-dione.

A reaction mixture consisting of 1.5 gm. (0.0287 mole) of 1-(3,5-di-O-toluoyl-2-deoxy-β-D-ribofuranosyl)-5-n-butyl-5,6-dihydro-s-triazine-2,4-

(1H,3H)-dione (prepared in Part B, above), 70 ml. methanol, and 0.4 ml. of a solution of 25% sodium methoxide in methanol is stirred for 18 hours at 22° C. Thin-layer chromatography (25% methanol in chloroform) indicates one spot with a Rf 0.7. At this time solid carbon dioxide chips are added until the pH of the solution is 7.0. The methanol is removed by evaporation under reduced pressure. The residue thus obtained is dispersed in a mixture consisting of 50 ml. chloroform and 100 ml. water. The aqueous phase is washed five times with chloroform. The layers are separated, and the water is evaporated under reduced pressure at 40° C. There is obtained 0.97 gm. of residue. The residue is placed on a prepacked E. Merck Silica-gel-60 Column, Type C. The column is developed with a solvent mixture consisting of 10 percent methanol in chloroform at the rate of 3 ml. per minute. Fractions containing desired material, i.e. those fractions indicating positive char with a 50% aqueous sulfuric acid spray, are collected and the solvent mixture is removed by evaporation under reduced pressure. There is thus obtained 0.632 gm. (76.7 percent yield) of preparation of 1-(2-deoxy-$\beta$-D-ribofuranosyl)-5-n-butyl-5,6-dihydro-s-triazine-2,4-(1H,3H)-dione as a clear glass.

Analysis: Calc'd for $C_{12}H_{21}N_2O_5$: C, 50.16; H, 7.37; N, 14.62. Found: C, 49.71; H, 7.17; N, 14.38.

EXAMPLE 4

Part A

Following the procedure described in Example 1, Part A, but substituting for the 5-ethyl-5,6-dihydro-s-triazine-2,4-(1H,3H)-dione,
3,4,5,6-tetrahydro-4-imino-s-triazine-2-(1H)-one,
3,4,5,6-tetrahydro-4-imino-5-methyl-s-traizine-2-(1H)-one,
3,4,5,6-tetrahydro-4-imino-5-ethyl-s-triazine-2-(1H)-one,
3,4,5,6-tetrahydro-4-imino-5-n-propyl-s-triazine-2-(1H)-one,
3,4,5,6-tetrahydro-4-imino-5-cyclopropyl-s-triazine-2-(1H)-one,
3,4,5,6-tetrahydro-4-imino-5-isopropyl-s-triazine-2-(1H)-one,
4-(acetylimino)-3,4,5,6-tetrahydro-s-triazine-2-(1H)-one,
4-(acetylimino)-3,4,5,6-tetrahydro-5-methyl-s-triazine-2-(1H)-one,
4-(acetylimino)-3,4,5,6-tetrahydro-5-ethyl-s-triazine-2-(1H)-one,
4-(acetylimino)-3,4,5,6-tetrahydro-5-n-propyl-s-triazine-2-(1H)-one,
4-(acetylimino)-3,4,5,6-tetrahydro-5-cyclopropyl-s-triazine-2-(1H)-one,
4-(acetylimino)-3,4,5,6-tetrahydro-5-isopropyl-s-triazine-2-(1H)-one,
5,6-dihydro-s-triazine-2,4-(1H,3H)-dione,
6-methyl-5,6-dihydro-s-triazine-2,4-(1H,3H)-dione,
5-cyclopropyl-5,6-dihydro-s-triazine-2,4-(1H,3H)-dione,
5-n-propyl-5,6-dihydro-s-triazine-2,4-(1H,3H)-dione,
5-isopropyl-5,6-dihydro-s-triazine-2,4-(1H,3H)-dione,
5-methoxymethyl-5,6-dihydro-s-triazine-2,4-(1H,3H)-dione,
5-methylthiomethyl-5,6-dihydro-s-triazine-2,4-(1H,3H)-dione, dione,
5-methyl-5,6-dihydro-2-thio-s-triazine-4-(1H,3H)-one,
5-ethyl-5,6-dihydro-2-thio-s-triazine-4-(1H,3H)-one, there are prepared the corresponding:
3,4,5,6-tetrahydro-4-imino-2-O-trimethylsilyl-s-triazine,
3,4,5,6-tetrahydro-4-imino-5-methyl-2-O-trimethylsilyl-s-triazine,
3,4,5,6-tetrahydro-4-imino-5-ethyl-2-O-trimethylsilyl-s-triazine,
3,4,5,6-tetrahydro-4-imino-5-n-propyl-2-O-trimethylsilyl-s-triazine,
3,4,5,6-tetrahydro-4-imino-5-cyclopropyl-2-O-trimethylsilyl-s-triazine,
3,4,5,6-tetrahydro-4-imino-5-isopropyl-2-O-trimethylsilyl-s-triazine,
4-(acetylimino)-3,4,5,6-tetrahydro-2-O-trimethylsilyl-s-triazine,
4-(acetylimino)-3,4,5,6-tetrahydro-5-methyl-2-O-trimethylsilyl-s-triazine,
4-(acetylimino)-3,4,5,6-tetrahydro-5-ethyl-2-O-trimethylsilyl-s-triazine,
4-(acetylimino)3,4,5,6-tetrahydro-5-n-propyl-2-O-trimethylsilyl-s-triazine,
4-(acetylimino)-3,4,5,6-tetrahydro-5-cyclopropyl-2-O-trimethylsilyl-s-triazine,
4-(acetylimino)-3,4,5,6-tetrahydro-5-isopropyl-2-O-trimethylsilyl-s-triazine,
5,6,-dihydro-2-O-trimethylsilyl-s-triazine-4-(3H)-one,
5,6-dihydro-6-methyl-2-O-trimethylsilyl-s-triazine-4-(3H)-one,
5,6-dihydro-5-cyclopropyl-2-O-trimethylsilyl-s-triazine-4-(3H)-one,
5,6-dihydro-5-n-propyl-2-O-trimethylsilyl-s-triazine-4-(3H)-one,
5,6-dihydro:5-isopropyl-2-O-trimethylsilyl-s-triazine-4-(3H)-one,
5,6-dihydro-5-methoxymethyl-2-O-trimethylsilyl-s-triazine-4-(3H)-one,
5,6-dihydro-5-methylthiomethyl-2-O-trimethylsilyl-s-triazine-4-(3H)-one,
5,6-dihydro-5-methyl-2-thio-trimethylsilyl-s-triazine-4-(3H)-one, and
5,6-dihydro-5-ethyl-2-thio-trimethylsilyl-s-triazine-4-(3H)-one respectively.

Part B

Following the procedure described in Example 1, Part B, but substituting
3,4,5,6-tetrahydro-4-imino-2-O-trimethylsilyl-s-triazine,
3,4,5,6-tetrahydro-4-imino-5-methyl-2-O-trimethylsilyl-s-triazine,
3,4,5,6-tetrahydro-4-imino-5-ethyl-2-O-trimethylsilyl-s-triazine,
3,4,5,6-tetrahydro-4-imino-5-n-propyl-2-O-trimethylsilyl-s-triazine,
3,4,5,6-tetrahydro-4-imino-5-cyclopropyl-2-O-trimethylsilyl-s-triazine,
3,4,5,6-tetrahydro-4-imino-5-isopropyl-2-O-trimethylsilyl-s-triazine,
4-(acetylimino)-3,4,5,6-tetrahydro-2-O-trimethylsilyl-s-triazine,
4-(acetylimino)-3,4,5,6-tetrahydro-5-methyl-2-O-trimethylsilyl-s-triazine,
4-(acetylimino)-3,4,5,6-tetrahydro-5-ethyl-2-O-trimethylsilyl-s-triazine,
4-(acetylimino)-3,4,5,6-tetrahydro-5-n-propyl-2-O-trimethylsilyl-s-triazine,
4-(acetylimino)-3,4,5,6-tetrahydro-5-cyclopropyl-2-O-trimethylsilyl-s-triazine, 4-(acetylimino)-3,4,5,6-tetrahydro-5-isopropyl-2-O-trimethylsilyl-s-triazine, 5,6-dihydro-2-O-trimethylsilyl-s-triazine-4-(3H)-one, 5,6,-dihydro-6-methyl-2-O-trimethylsilyl-s-triazine-4-(3H)-one, 5,6-dihydro-5-cyclopropyl-2-O-trimethylsilyl-s-triazine-4-(3H)-one, 5,6-dihydro-5-n-propyl-2-O-trimethylsilyl-s-triazine-4-(3H)-one, 5,6-dihydro-5-isopropyl-2-O-trimethylsilyl-s-triazine-4-(3H)-one, 5,6-dihydro-5-methoxymethyl-2-O-trimethylsilyl-s-triazine-4-(3H)-one, 5,6-dihydro-5-methylthiomethyl-2-O-trimethylsilyl-s-triazine-4-(3H)-one, 5,6-dihydro-5-methyl-2-thio-trimethylsilyl-s-triazine-4-(3H)-one, and 5,6,-dihydro-5-ethyl-2-thio-trimethylsilyl-s-triazine-4-(3H)-one respectively, for the 5-ethyl-5,6-dihydro-2-O-(trimethylsilyl)-s-triazine-4-(3H)-one, there are prepared the corresponding:

1-(2-deoxy-3,5-di-O-toluoyl-β-D-ribofuranosyl)-4-imino-3,4,5,6-tetrahydro-s-triazine-2-(1H)-one, 1-(2-deoxy-3,5-di-O-toluoyl-β-D-ribofuranosyl)-4-imino-3,4,5,6-tetrahydro-5-methyl-s-triazine-2-(1H)-one, 1-(2-deoxy-3,5-di-O-toluoyl-β-D-ribofuranosyl)-4-imino-3,4,5,6-tetrahydro-5-ethyl-s-triazine-2-(1H)-one, 1-(2-deoxy-3,5-di-O-toluoyl-β-D-ribofuranosyl)-4-imino-3,4,5,6-tetrahydro-5-n-propyl-s-triazine-2-(1H)-one, 1-(2-deoxy-3,5-di-O-toluoyl-β-D-ribofuranosyl)-4-imino-3,4,5,6-tetrahydro-5-cyclopropyl-s-triazine-2-(1H)-one, 1-(2-deoxy-3,5-di-P-toluoyl-β-D-ribofuranosyl)-4-imino-3,4,5,6-tetrahydro-5-isopropyl-s-triazine-2-(1H)-one, 1(2-deoxy-3,5-di-O-toluoyl-β-D-ribofuranosyl)-4-(acetylimino)-3,4,5,6-tetrahydro-s-triazine-2-(1H)-one 1-(2-deoxy-3,5-di-O-toluoyl-β-D-ribofuranosyl)-4-(acetylimino)-3,4,5,6-tetrahydro-5-methyl-s-triazine-2-(1H)-one, 1-(2-deoxy-3,5-di-O-toluoyl-β-D-ribofuranosyl)-4-(acetylinimo)-3,4,5,6-tetrahydro-5-ethyl-s-triazine-2-(1H)-one, 1-(2-deoxy-3,5-di-O-toluoyl-β-D-ribofuranosyl)-4-(acetylimino)-3,4,5,6-tetrahydro-5-n-propyl-s-triazine-2-(1H)-one, 1-(2-deoxy-3,5-di-O-toluoyl-β-D-ribofuranosyl)-4-(acetylimino)-3,4,5,6-tetrahydro-5-cyclopropyl-s-triazine-2-2-(1H)-one, 1(2-deoxy-3,5-di-O-toluoyl-β-D-ribofuranosyl)-4-(acetylimino)3,4,5,6-tetrahydro-5-isopropyl-s-triazine-2;1 -(1H)-one, 1(2-deoxy-3,5-di-O-toluoyl-β-D-ribofuranosyl)-5,6-dihydro-s-triazine-2,4-(1H,3H)-dione, 1(2-deoxy-3,5-di-O-toluoyl-β-D-ribofuranosyl)-5,6-dihydro-6-methyl-s-triazine-2,4-(1H,3H)-dione, 1-(2-deoxy-3,5-di-O-toluoyl-β-D-ribofuranosyl)-5,6-dihydro-5-cyclopropyl-s-triazine-2,4-(1H,3H)-dione.

1-(2-deoxy-3,5-di-O-toluoyl-β-D-ribofuranosyl)-5,6-dihydro-5-n-propyl-s-triazine-2,4-(1H,3H)-dione, 1-(2-deoxy-3,5-di-O-toluoyl-β-D-ribofuranosyl)-5,6-dihydro-5-isopropyl-s-triazine-2,4-(1H,3H)-dione, 1-(2-deoxy-3,5-di-O-toluoyl-β-D-ribofuranosyl)-5,6-dihydro-5-methoxymethyl-s-triazine-2,4-(1H,3H)-dione, 1-(2-deoxy-3,5-di-O-toluoyl-β-D-ribofuranosyl)-5,6-dihydro-5-methylthiomethyl-s-triazine-2,4-(1H,3H)-dione, 1-(2-deoxy-3,5-di-O-toluoyl-β-D-ribofuranosyl)-5,6-dihydro-5-methyl-2-thio-s-triazine-4-(1H,3H)-one, and H)-one, 1-(2-deoxy-3,5-di-O-toluoyl-β-D-ribofuranosyl)-5,6-dihydro-5-ethyl-2-thio-s-triazine-4-(1H,3H)-one, respectively.

Part C

Following the procedure described in example 1, Part C, but substituting 1-(2-deoxy-3,5-di-O-toluoyl-β-D-ribofuranosyl)-4-imino-3,4,5,6-tetrahydro-s-triazine-2-(1H)-one, 1-(2-deoxy-3,5-di-O-toluoyl-β-D-ribofuranosyl)-4-imino-3,4,5,6-tetrahydro-5-methyl-s-triazine-2-(1H)-one, 1-(2-deoxy-3,5-di-O-toluoyl-β-D-ribofuranosyl)-4-imino-3,4,5,6-tetrahydro-5-ethyl-s-triazine-2-(1H)-one, 1-(2-deoxy-3,5-di-O-toluoyl-β-D-ribofuranosyl)-4-imino-3,4,5,6-tetrahydro-5-n-propyl-s-triazine-2-one, 1-(2-deoxy-3,5-di-O-toluoyl-β-D-ribofuranosyl)-4-imino-3,4,5,6-tetrahydro-5-cyclopropyl-s-triazine-2-(1H)-one, 1-(2-deoxy-3,5-di-O-toluoyl-β-D-ribofuranosyl)-4-imino-3,4,5,6-tetrahydro-5-isopropyl-s-triazine-2-(1H)-one, 1-(2-deoxy-3,5-di-O-toluoyl-β-D-ribofuranosyl)-4-(acetylimino)-3,4,5,6-tetrahydro-s-triazine-2-(1H)-one, 1-(2-deoxy-3,5-di-O-toluoyl-β-D-ribofuranosyl)-4-acetylimino)- 3,4,5,6-tetrahydro-5-methyl-s-triazine-2-(1H)-one, 1-(2-deoxy-3,5-di-O-toluoyl-β-D-ribofuranosyl)-4-(acetylimino)-3,4,5,6-tetrahydro-5-ethyl-s-triazine-2-(1H)-one, 1-(2-deoxy-3,5-di-O-toluoyl-β-D-ribofuranosyl)-4-(acetylimino)-3,4,5,6-tetrahydro-5-n-propyl-s-triazine-2-(1H)-one, 1-(2-deoxy-3,5-di-O-toluoyl-β-D-ribofuranosyl(-4-(acetylimino)-3,4,5,6-tetrahydro-5-cyclopropyl-s-triazine-2-(1H)-one, 1-(2-deoxy-3,5-di-O-toluoyl-β-D-ribofuranosyl)-4-(acetylimino)-3,4,5,6-tetrahydro-5-isopropyl-s-(1H)-one, 1-(2-deoxy-3,5-di-O-toluoyl-β-D-ribofuranosyl)-5,6-dihydro-s-triazine-2,4-(1H,3H)-dione, 1-(2-deoxy-3,5-di-O-toluoyl-β-D-ribofuranosyl)-5,6-dihydro-6-methyl-s-triazine-2,4-(1H,3H)-dione, 1-(2-deoxy-3,5-di-O-toluoyl-β-D-ribofuranosyl)-5,6-dihydro-5-cyclopropyl-s-triazine-2,4-(1H,3H)-dione, 1-(2-deoxy-3,5-di-O-toluoyl-β-D-ribofuranosyl)-5,6-dihydro-5-n-propyl-s-triazine-2,4-(1H,3H)-dione, 1-(2-deoxy-3,5-di-O-toluoyl-β-D-ribofuranosyl)-5,6-dihydro-5-isopropyl-s-triazine-2,4-(1H,3H)-dione, 1-(2-deoxy-3,5-di-O-toluoyl-β-D-ribofuranosyl)-5,6-dihydro-5-methoxymethyl-s-triazine-2,4-(1H,3H)-dione, 1-(2-deoxy-3,5-di-O-toluoyl-β-D-ribofuranosyl)-5,6-dihydro-5-methylthiomethyl-s-triazine-2,4-(1H,3H)-dione, 1-(2-deoxy-3,5-di-O-toluoyl-β-D-ribofuranosyl)-5,6-dihydro-5-methyl-2-thio-s-triazine-4-(1H,3H)-one, and 1-(2-deoxy-3,5-di-O-toluoyl-β-D-ribofuranosyl)-5,6-dihydro-5-ethyl-2-thio-s-triazine-4-(1H,3H)-one, for the 1- (2-deoxy-3,5-di-O-toluoyl-β-D-ribofuranoyl)-5-ethyl-5,6-dihydro-s-triazine-2,4-(1H,3H)-dione, there are prepared the corresponding:

1-(2-deoxy-β-D-ribofuranosyl)-4-imino-3,4,5,6-tetrahydro-s-triazine-2-(1H)-one, 1-(2-deoxy-β-D-ribofuranosyl)-4-imino-5-methyl-3,4,5,6-tetrahydro-s-triazine-2-(1H)-one, 1-(2-deoxy-β-D-ribofuranosyl)-4-imino-5-ethyl-3,4,5,6-tetrahydro-s-triazine-2-(1H)-one, 1-(2-deoxy-β-D-ribofuranosyl)-4-imino-5-n-propyl-3,4,5,6-tetrahydro-s-triazine-2-(1H)-one, 1-(2-deoxy-β-D-ribofuranosyl)-4-imino-5-cyclopropyl-3,4,5,6-tetrahydro-s-triazine-2-(1H)-one, 1-(2-deoxy-β-D-ribofuranosyl)-4-imino-5-isopropyl-3,4,5,6-tetrahydro-s-triazine-2-(1H)-one, 1-(2-deoxy-β-D-ribofuranosyl)-5,6-dihydro-s-triazine-2,4-(1H,3H)-dione, 1-(2-deoxy-β-D-ribofuranosyl)-5,6-dihydro-6-methyl-s-triazine-2,4-(1H,3H)-dione, 1-(2-deoxy-β-D-ribofuranosyl)-5,6-dihydro-5-cyclopropyl-s-triazine-2,4-(1H,3H)-dione, 1-(2-deoxy-β-D-ribofuranosyl)-5,6-dihydro-5-n-propyl-s-triazine-2,4-(1H,3H)-dione, 1-(2-deoxy-β-D-ribofuranosyl)-5,6-dihydro-5-isopropyl-s-triazine-2,4-(1H,3H)-dione, 1-(2-deoxy-β-D-ribofuranosyl)-5,6-dihydro-5-methoxymethyl-s-triazine-2,4-(1H,3H)-dione, 1-(2-deoxy-β-D-ribofuranosyl)-5,6-dihydro-5-methylthio-s-triazine-2,4-(1H,3H)-dione, 1-(2-deoxy-β-D-ribofuranosyl)-5,6-dihydro-5-methyl-2-thio-s-triazine-4-(1H,3H)-one, and 1-(2-deoxy-β-D-ribofuranosyl)-5,6-dihydro-5-ethyl-2-thio-s-triazine-4-(1H,3H)-one.

EXAMPLE 5

Following the procedure described in Example 1, Part B, but substituting 1-(2-deoxy-3,5-di-O-acetyl-D-ribofuranosyl)-chloride, 1-(2-deoxy-3,5-di-O-toluoyl-D-ribofuranosyl)-bromide, 1-(2-deoxy-3,5-di-O-benzoyl-D-ribofuranosyl)-chloride, 1-(2-deoxy-3,5-di-O-p-nitrobenzoyl-D-ribofuranosyl)-chloride, 1-(2-deoxy-3,5-di-O-p-chlorobenzoyl-D-ribofuranosyl)-chloride, 1-(2-deoxy-3,5-di-O-toluoyl-D-xylofuranosyl)-chloride for the 1-(2-deoxy-3,5-di-O-toluoyl-D-ribofuranosyl)-chloride, there are prepared the corresponding:

1-(2-deoxy-3,5-di-O-acetyl-β-D-ribofuranosyl)-5-ethyl-5,6-dihydro-s-triazine-2,4-(1H,3H)-dione, 1-(2-deoxy-3,5-di-O-toluoyl-β-D-ribofuranosyl)-5-ethyl-5,6-dihydro-s-triazine-2,4-(1H,3H)-dione, 1-(2-deoxy-3,5-di-O-benzoyl-β-D-ribofuranosyl)-5-ethyl-5,6-dihydro-s-triazine-2,4-(1H,3H)-dione, 1-(2-deoxy-3,5-di-O-p-nitrobenzoyl-β-D-ribofuranosyl)-5-ethyl-5,6-dihydro-s-triazine-2,4-(1H,3H)-dione, 1-(2-deoxy-3,5-di-O-p-chlorobenzoyl-β-D-ribofuranosyl)-5-ethyl-5,6-dihydro-s-trizine-2,4-(1H,3H)-dione, and 1-(2-deoxy-3,5-di-O-toluoyl-β-D-xylofuranosyl)-5-ethyl-5,6-dihydro-s-triazine-2,4-(1H,3H)-dione, respectively.

The 1-(2-deoxy-β-D-pentofuranosyl)-5,6-dihydro-4-imino-s-triazine-2-(1H,3H)-ones and thiones of this invention (compounds according to Formula Ia wherein X is imino) form acid addition salts with acids, for example, hydrochloric, sulfuric, phosphoric, benzoic, acetic, propionic, picric, citric, succinic, maleic, tartaric, thiocyanuric, and fluosilicic acid. Such acid addition salts are useful for purifying the free base compounds and for metathetic reactions to form still other acid addition salts. The acid addition salts have sometimes advantageous solubility properties over the free bases.

EXAMPLE 6

Preparation of 1-(2-deoxy-3-lauroyl-β-D-ribofuranosyl)-5,6-dihydro-5-methyl-s-triazine-2,4-(1H,3H)-dione Part A 1-(5-tert-butyldimethylsilyl-2-deoxy-β-D-ribofuranosyl)-5-methyl-5,6-dihydro-s-triazine-2,4-(1H,3H)-dione.

A reaction mixture consisting of 12.25 gm. (0.050 mole) of 1-(2-deoxy-β-D-ribofuranosyl)-5,6-dihydro-5-methyl-s-triazine-2,4-(1H,3H)-dione, 50 ml. dimethylformamide, and 8.5 gm. (0.125 mole) of imidazole was warmed to 35° C. and stirred until the imidazole had dissolved. There was then added with continued stirring 7.55 gm. (0.050 mole) tert-butyldimethylsilyl chloride. Stirring was continued for 18 hours at 35° C. The solvent medium was then removed by evaporation under reduced pressure, and the residue thus obtained was dispersed in a solvent mixture consisting of 200 ml. chloroform and 50 ml. water. The two phases were allowed to stabilize and the aqueous phase was recovered. It was washed two times with 50 ml. portions of chloroform. The three chloroform layers (original and two washes) were combined and washed with three-25 ml. portions of water. The washed chloroform solution was dried over anhydrous magnesium sulfate and filtered. The chloroform was then removed by evaporation under reduced pressure to give 14.8 gm. (82.5% yield) of 1-(5-tert-butyldimethylsilyl-2-deoxy-β-D-ribofuranosyl)-5,6-dihydro-5-methyl-s-triazine-2,4-(1H,3H)-dione.

Part B 1-(5-tert-butyldimethylsilyl-3-lauroyl-2-deoxy-β-D-ribofuranosyl)-5,6-dihydro-5-methyl-s-triazine-2,4-(1H,3H)-dione.

To a solution consisting of 3.59 gm. (0.010 mole) of 1-(5-tert-butyldimethylsilyl-2-deoxy-β-D-ribofuranosyl)-5-methyl-5,6-dihydro-s-triazine-2,4-(1H,3H)-dione and 30 ml. A.R. pyridine that had been cooled to 5° C. was added, with stirring, 2.55 gm. (0.0116 mole) of freshly distilled lauroyl chloride. This reaction mixture was stirred for 18 hours at 25° C. Then it was cooled to 10° C. and 3 ml. water was added. This mixture was stirred at 25° C. while the solvents were removed by evaporation under reduced pressure. The residue thus obtained was dispersed in a solvent mixture consisting of 100 ml. chloroform and 50 ml. saturated aqueous sodium bicarbonate. The aqueous and organic phases were allowed to stabilize and the organic phase was saved. It was washed two times with 50 ml. portions of saturated aqueous sodium bicarbonate and dried over anhydrous magnesium sulfate. The dried chloroform solution was filtered and the filter was washed with chloroform. The filtrate and washings were combined and the chloroform was removed by evaporation under reduced pressure. There was thus obtained 4.8 gm. (88.7% yield) of 1-(5-tert-butyldimethylsilyl-3-lauroyl-2-deoxy-β-D-ribofuranosyl)-5,6-dihydro-5-methyl-s-triazine-2,4-(1H,3H)-dione.

Following the same procedure, but substituting 1-(2-deoxy-β-D-ribofuranosyl)-5-ethyl-5,6-dihydro-s-triazine-2,4-(1H,3H)-dione, 1-(2-deoxy-β-D-ribofuranosyl)-5-n-butyl-5,6-dihydro-s-triazine-2,4-(1H,3H)-dione, 1-(2-deoxy-β-D-ribofuranosyl)-5-n-propyl-5,6-dihydro-s-triazine-2,4-(1H,3H)-dione, 1-(2-deoxy-β-D-ribofuranosyl)-5-cyclopropyl-5,6-dihydro-s-triazine-2,4-(1H,3H)-dione, and 1-(2-deoxy-β-D-ribofuranosyl)-3,4,5,6-tetrahydro-4-imino-5-methyl-s-triazine-2-(1H)-one for the 1-(5-tert-butyldimethylsilyl-2-deoxy-β-D-ribofuranosyl)-5,6-dihydro-5-methyl-s-triazine-2,4-(1H,3H)-dione there are prepared the corresponding:

1-(2-deoxy-5-lauroyl-β-D-ribofuranosyl)-5-ethyl-5,6-dihydro-s-triazine-2,4-(1H,3H)-dione, 1-(2-deoxy-5-lauroyl-β-D-ribofuranosyl)-5-n-butyl-5,6-dihydro-s-triazine-2,4-(1H,3H)-dione, 1-(2-deoxy-5-lauroyl-β-D-ribofuranosyl)-5,6-dihydro-5-n-propyl-s-triazine-2,4-(1H,3H)-dione, 1-(2-deoxy-5-lauroyl-β-D-ribofuranosyl)-5-cyclopropyl-5,6-dihydro-s-triazine-2,4-(1H,3H)-dione, and 1-(2-deoxy-5-lauroyl-β-D-ribofuranosyl)-4-imino-5-methyl-3,4,5,6-tetrahydro-s-triazine-2-(1H)-one, respectively.

Part C

Object compound 1-(2-deoxy-3-lauroyl-β-D-ribofuranosyl)-5,6-dihydro-5-methyl-s-triazine-2,4-(1H,3H)-dione.

A reaction mixture consisting of 4.8 gm. (0.009 mole) of 2-(5-tert-butyldimethlysilyl-3-lauroyl-2-deoxy-β-D-ribofuranosyl)-5,6-dihydro-5-methyl-s-triazine-2,4-(1H,3H)-dione, 26 ml. tetrahydrofuran, and 28 ml. tetra-n-butyl ammonium floride in tetrahydrofuran was allowed to stand for 18 hours at 25° C. The medium was then removed by evaporation under reduced pressure, and the residue thus obtained was dissolved in 200 ml. chloroform. The chloroform solution was washed with two-50 ml. portions of saturated aqueous sodium bicarbonate and three-50 ml. portions water, and then dried over anhydrous magnesium sulfate. The washed chloroform solution was filtered and the residue was washed with additional chloroform which was added to the filtrate. The chloroform was then removed by evaporation under reduced pressure to give a semi-solid residue. This residue was dissolved in 25 ml. acetone and technical hexane was added to the acetone solution until it became cloudy. After seeding, the cloudy solution was allowed to crystallize for 18 hours at 25° C. The crystals were collected on a filter and washed with a mixture of acetone and technical hexane. There was thus obtained 1.41 gm. of 1-(2-deoxy-3-lauroyl-β-D-ribofuranosyl)-5,6-dihydro-5-methyl-s-triazine-2,4-(1H,3H)-dione. An analytical sample was prepared by recrystallizing 1.4 gm. from a mixture of 20 ml. acetone and 25 ml. hexane. It weighed 1.15 gm. and had a melting point at 136° C. to 137° C.

Analysis:
Calc'd for $C_{21}H_{37}N_3O_6$:
C, 58.99; H, 8.72; N, 9.82.
Found: C, 58.83; H, 8.98; N, 9.43.

IR: OH: 3480 cm$^{-1}$;
NH: 3200, 3080;
C=O: 1740, 1710, 1695, and 1685;
BNH/Other: 1520;
C—O/C—N: 1270, 1165, 1105;
Other: 725.

The following is a comparative test of 1-(2-deoxy-β-D-ribofuranosyl)-5-ethyl-5,6-dihydro-s-triazine-2,4-(1H,3H)-dione, U-50,365 and 1-(2-deoxy-β-D-ribofuranosyl)-5-methyl-5,6-dihydro-s-triazine-2,4-(1H,3H)-dione, U-44,590. Mean survial time (MST) in days and per ant survivors (% s) is given. The compounds are administered subcutaneously to mice which are inoculated intravenously with $3 \times 10^5$ PFM (MRS) Herpes simplex virus (HSV-1). Treatment is initiated one hour after virus inoculation and is followed by treatment three times daily for five consecutive days. A detailed account of the materials, methods and results are as follows.

Male mice, weighing approximately 18 gm. each, are divided into eight groups of 20. Group 1 is treated with Sterile saline, group 2 with 400 mg./kg./dose (mkd) U-44,590, group 3 with 200 mkd U-44,590, group 4 with 100 mkd U-44,590, group 5 with 50 mkd U-44,590, group 6 with 200 mkd U-50,365, group 7 with 100 mkd U-50,365, and group 8 with 50 mkd U-50,365. The test compound is dissolved in Sterile saline and administered subcutaneously in the nape of the neck at 8:00 a.m., 12:00 noon, and 4:00 p.m. on days 1, 2, 3 and 4. $3 \times 10^5$ PFU (MRS) Herpes simplex virus (HSV-1) is inoculated into the tail vein at 8:00 a.m. on day 0. On day 0, the test compound is given at 9:00 a.m., 12:00 noon, and 4:00 p.m. Death and paralysis are recorded daily.

Hind leg paralysis usually preceeded death by 1-2 days. All mice died that became paralyzed. Death pattern of the 8 groups, as shown in the Figure illustrates the dose response obtained.

In addition to its antiviral activity, U-50,365 is less cytotoxic than U-44,590 and as determined by Standard microbiological disk plate assays did not exhibit antibacterial activity against *Bacillus subtilis, Staphylococcus aureus, Sarcina lutea, Klebsiella pneumoniae, Escherichia coili, Salmonella schottmulleri, Proteus vulgaris, Mycobacterium avium, Penicillium oxalicum, Saccharomyces pastorianus Pseudomonas aeruginosa* or *Pseudomonas fluorescens* with assay disks treated with 20 microliters of a 1 mg./ml. aqueous solution of U-50,365.

We claim:
1. A compound of the formula:

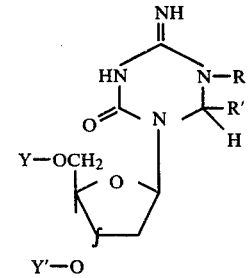

wherein R' is selected from the group consisting of hydrogen and lower-alkyl; Y is selected from the group consisting of hydrogen, carboxacyl of from 1 through 18 carbon atoms, and phosphono; Y' is selected from the group consisting of carboxacyl of 1 through 18 and hydrogen; R is selected from the group consisting of hydrogen, lower-alkyl, phenyl, benzyl, cyclopropyl, lower-alkoxylower-alkyl, and lower-alkylthiolower-alkyl; and pharmaceutically acceptable salts thereof.

2. A compound of the formula:

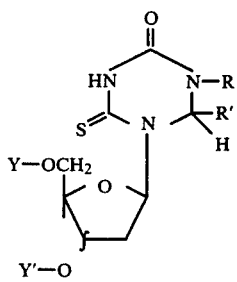

wherein R' is selected from the group consisting of hydrogen and lower-alkyl; Y is selected from the group consisting of hydrogen, carboxacyl of from 1 through 18 carbon atoms, and phosphono; Y' is selected from the group consisting of carboxacyl of 1 through 18 and hydrogen: R is selected from the group consisting of hydrogen, lower-alkyl, phenyl, benzyl, cyclopropyl, lower-alkoxylower-alkyl, and lower-alkylthiolower-alkyl; and pharmaceutically acceptable salts thereof.

3. A compound of the formula:

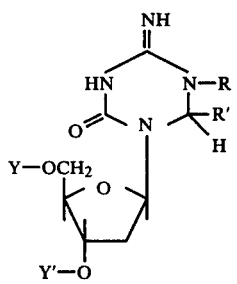

wherein R is selected from the group consisting of hydrogen, lower alkyl of 1 through 4 carbon atoms and cyclopropyl; R' is selected from the group consisting of hydrogen and lower alkyl of 1 through 4 carbon atoms; Y is selected from the group consisting of hydrogen, carboxacyl of from 1 through 18 carbon atoms, and phosphono; Y' is selected from the group consisting of carboxacyl of from 1 through 18 carbon atoms and hydrogen; and pharmaceutically acceptable salts thereof.

4. A compound according to claim 3 wherein R' is hydrogen.

5. A compound according to claim 3 wherein Y and Y' are hydrogen.

6. A compound according to claim 3 wherein Y, Y' and R' are hydrogen.

7. A compound according to claim 3 wherein Y and Y' are carboxacyl of from 1 through 18 carbon atoms and R' is hydrogen.

8. A compound according to claim 3 wherein Y is carboxacyl of from 1 through 18 carbon atoms, and Y' and R' are hydrogen.

9. A compound according to claim 3 wherein Y' is carboxacyl of from 1 through 18 carbon atoms; and Y and R' are hydrogen.

10. A compound of the formula

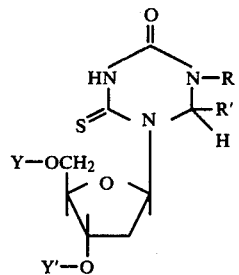

wherein R is selected from the group consisting of hydrogen, lower alkyl of 1 through 4 carbon atoms, and cyclopropyl; R' is selected from the group consisting of hydrogen and lower alkyl of 1 through 4 carbon atoms; Y is selected from the group consisting of hydrogen, carboxacyl of from 1 through 18 carbon atoms, and phosphono; and Y' is selected from the group consisting of carboxacyl of from 1 through 18 carbon atoms and hydrogen; and pharmaceutically acceptable salts thereof.

11. A compound according to claim 10 wherein R' is hydrogen.

12. A compound according to claim 10 wherein Y and Y' are hydrogen.

13. A compound according to claim 10 wherein Y, Y' and R' are hydrogen.

14. A compound according to claim 10 wherein Y and Y' are carboxacyl of from 1 through 18 carbon atoms and R' is hydrogen.

15. A compound according to claim 10 wherein Y is carboxacyl of from 1 through 18 carbon atoms, and Y' and R' are hydrogen 16. A compound according to claim 10 wherein Y' is carboxacyl of from 1 through 18 carbon atoms; and Y and R' are hydrogen.

17. 1-(2-Deoxy-$\beta$-D-ribofuranosyl)-5-ethyl-5,6-dihydro-s-triazine-2,4-(1H,3H)-dione.

18. 1-(2-Deoxy-$\beta$-D-ribofuranosyl)-5-n-butyl-5,6-dihydro-s-triazine-2,4-(1H,3H)-dione.

* * * * *

UNITED STATES PATENT OFFICE
CERTIFICATE OF CORRECTION

Patent No. 4,171,431                    Dated October 16, 1979

Inventor(s) Harvey I. Skulnick

It is certified that error appears in the above-identified patent and that said Letters Patent are hereby corrected as shown below:

Front page [56] References Cited: line 2: "Vorbruggan" should read --Vorbruggen--; line 4: "Vorbruggan" should read --Vorbruggen--; line 6: "DoBoa" should read --DeBoer--.
Column 1, line 27: "johnson" should read --Johnson--.
Column 6, line 4: "riboruranosyl" should read --ribofuranosyl--.
Column 6, line 6: "ribofuranoxyl" should read --ribofuranosyl--.
Column 6, line 14: "mg./kg.day" should read --mg./kg./day--.
Column 6, line 15: "mg./kg.day" should read --mg./kg./day--.
Column 8, line 15: "alkylof" should read --alkyl of--.
Column 9, lines 26-27: "lower-alkoxy lower-alkyl" should read --lower-alkoxylower-alkyl--.
Column 9, line 59: "pentofuransyl" should read --pentofuranosyl--.
Column 11, line 20: "dihydros-" should read --dihydro-s- --.
Column 12, lines 51-52: "reaction is" should read --reaction mixture is--.
Column 14, line 5: "pecursor" should read --precursor--.
Column 14, line 51: "-5azauracil" should read -- -5-azauracil--.
Column 14, line 58: "5,6-dihyro-" should read --5,6-dihydro- --.
Column 15, line 24: "and chloroform" should read --in chloroform--.
Column 15, line 29: "5.6-" should read --5,6- --.
Column 15, line 33: "H, 4,86;" should read --H, 4.86;--.
Column 15, line 36: ";b 5,6-" should read --5,6- --.
Column 15, line 54: "(1;H," should read --(1H,--.
Column 17, line 10: "p-tolyoyl" should read --p-toluoyl--.
Column 17, line 60: "dihydro-20-" should read --dihydro-2-0- --.
Column 18, line 12: "3,5-di-0--" should read --3,5-di-0- --.
Column 20, line 15: "dione.)" should read --dione.--.
Column 20, line 46: "Th crystals" should read --The crystals--.
Column 22, line 7: "dihydro-20-" should read --dihydro-2-0- --.
Column 22, line 43: "[e." should read --[E.--.
Column 23, line 67: "dione, dione," should read --dione,--.
Column 25, line 37: "3,5-di-P-" should read --3,5-di-0- --.
Column 25, line 47: "(acetylinimo)-" should read --(acetylimino)- --.

UNITED STATES PATENT OFFICE
CERTIFICATE OF CORRECTION

Patent No. 4,171,431                              Dated  October 16, 1979

Inventor(s)  Harvey I. Skulnick

It is certified that error appears in the above-identified patent and that said Letters Patent are hereby corrected as shown below:

Column 25, line 54:  "triazine-2-2-" should read --triazine-2- --.
Column 25, line 57:  "zine-2;1-" should read --zine-2- --.
Column 26, lines 8-9:  "one, and H)-one," should read --one, and--.
Column 26, line 26:  "-2-one," should read -- -2-(1H)-one,--.
Column 30, line 36:  "as shown in the Figure illustrates" should read -- as shown in the curves of Table 1, illustrates --.

Column 30, line 43:  "coili" should resd -- coli --.

Signed and Sealed this

Twelfth  Day of  March 1985

[SEAL]

Attest:

DONALD J. QUIGG

Attesting Officer       Acting Commissioner of Patents and Trademarks